United States Patent
Newman

(10) Patent No.: US 10,430,833 B2
(45) Date of Patent: *Oct. 1, 2019

(54) SENSOR SURFACE OBJECT DETECTION METHODS AND SYSTEMS

(71) Applicant: NIO USA, INC., San Jose, CA (US)

(72) Inventor: Austin L. Newman, San Jose, CA (US)

(73) Assignee: NIO USA, Inc., San Jose, CA (US)

(*) Notice: Subject to any disclaimer, the term of this patent is extended or adjusted under 35 U.S.C. 154(b) by 178 days.

This patent is subject to a terminal disclaimer.

(21) Appl. No.: 15/394,425

(22) Filed: Dec. 29, 2016

(65) Prior Publication Data
US 2018/0143298 A1 May 24, 2018

Related U.S. Application Data

(60) Provisional application No. 62/424,976, filed on Nov. 21, 2016.

(51) Int. Cl.
*G06Q 30/02* (2012.01)
*G06F 16/95* (2019.01)
(Continued)

(52) U.S. Cl.
CPC .......... *G06Q 30/0266* (2013.01); *A61B 5/01* (2013.01); *A61B 5/024* (2013.01); *A61B 5/08* (2013.01);
(Continued)

(58) Field of Classification Search
CPC ..... G01S 2007/4039; G01S 2007/4043; G01S 7/40; G01S 7/4004; G01S 7/4008;
(Continued)

(56) References Cited

U.S. PATENT DOCUMENTS 7,838,836 B2* 11/2010 Robert ................ B60Q 1/0023
250/341.7
9,449,561 B1* 9/2016 Umansky ............... G09G 5/003
(Continued)

FOREIGN PATENT DOCUMENTS

WO WO 2014/054124 4/2014

OTHER PUBLICATIONS

Davies, "This NIO EP9 performance EV wants to be the Tesla of Supercars," SlashGear, 2016, retrieved from https//www.slashgear.com/nextev-nio-ep9-car-tesla-of-performance-evs-21464829, 9 pages.
(Continued)

*Primary Examiner* — Thomas E Worden
(74) *Attorney, Agent, or Firm* — Sheridan Ross P.C.

(57) ABSTRACT

Methods, devices, and systems of a sensor surface object detection system are provided. Output from sensors of a vehicle may be used to describe an environment around the vehicle. In the event that a sensor is obstructed by dirt, debris, or detritus the sensor may not sufficiently describe the environment for autonomous control operations. The sensor surface object detection system may receive output from the sensors of the vehicle to determine whether any of the sensors are obstructed. The determination may be made by comparing the output of one sensor to another, determining whether the output of a sensor is within a predetermined threshold, or comparing characteristics of multiple sensor outputs to one another. When a sensor is determined to be obstructed, the system may send a command to a cleaning system to automatically remove the obstruction.

13 Claims, 15 Drawing Sheets

(51) Int. Cl.
| | |
|---|---|
| G06F 16/29 | (2019.01) |
| A61B 5/01 | (2006.01) |
| A61B 5/024 | (2006.01) |
| A61B 5/08 | (2006.01) |
| A61B 5/16 | (2006.01) |
| A61B 5/18 | (2006.01) |
| B60R 11/04 | (2006.01) |
| B60S 1/62 | (2006.01) |
| B60W 10/04 | (2006.01) |
| B60W 10/18 | (2012.01) |
| B60W 10/20 | (2006.01) |
| B60W 30/09 | (2012.01) |
| B60W 40/04 | (2006.01) |
| B60W 40/08 | (2012.01) |
| B60W 40/09 | (2012.01) |
| B60W 40/105 | (2012.01) |
| B60W 50/00 | (2006.01) |
| B60W 50/08 | (2012.01) |
| B62D 15/02 | (2006.01) |
| G01C 21/34 | (2006.01) |
| G01C 21/36 | (2006.01) |
| G01S 7/40 | (2006.01) |
| G01S 7/497 | (2006.01) |
| G01S 13/86 | (2006.01) |
| G01S 13/87 | (2006.01) |
| G01S 15/02 | (2006.01) |
| G01S 17/89 | (2006.01) |
| G02B 27/00 | (2006.01) |
| G05D 1/00 | (2006.01) |
| G05D 1/02 | (2006.01) |
| G08G 1/16 | (2006.01) |
| G01S 13/93 | (2006.01) |
| B62D 15/00 | (2006.01) |

(52) U.S. Cl.
CPC ............... *A61B 5/165* (2013.01); *A61B 5/18* (2013.01); *B60R 11/04* (2013.01); *B60S 1/62* (2013.01); *B60W 10/04* (2013.01); *B60W 10/18* (2013.01); *B60W 10/20* (2013.01); *B60W 30/09* (2013.01); *B60W 40/04* (2013.01); *B60W 40/08* (2013.01); *B60W 40/09* (2013.01); *B60W 40/105* (2013.01); *B60W 50/0097* (2013.01); *B60W 50/0098* (2013.01); *B60W 50/08* (2013.01); *B60W 50/082* (2013.01); *B62D 15/00* (2013.01); *B62D 15/0265* (2013.01); *G01C 21/3407* (2013.01); *G01C 21/3461* (2013.01); *G01C 21/3469* (2013.01); *G01C 21/3484* (2013.01); *G01C 21/3492* (2013.01); *G01C 21/3682* (2013.01); *G01C 21/3691* (2013.01); *G01C 21/3697* (2013.01); *G01S 7/4021* (2013.01); *G01S 7/497* (2013.01); *G01S 13/862* (2013.01); *G01S 13/865* (2013.01); *G01S 13/867* (2013.01); *G01S 13/87* (2013.01); *G01S 15/02* (2013.01); *G01S 17/89* (2013.01); *G02B 27/0006* (2013.01); *G05D 1/0061* (2013.01); *G05D 1/0088* (2013.01); *G05D 1/0212* (2013.01); *G05D 1/0214* (2013.01); *G05D 1/0221* (2013.01); *G05D 1/0276* (2013.01); *G06F 16/29* (2019.01); *G06F 16/95* (2019.01); *G06Q 30/0269* (2013.01); *G08G 1/161* (2013.01); *G08G 1/163* (2013.01); *G08G 1/164* (2013.01); *G08G 1/165* (2013.01); *G08G 1/166* (2013.01); *B60W 2040/0809* (2013.01); *B60W 2050/0004* (2013.01); *B60W 2050/0014* (2013.01); *B60W 2300/34* (2013.01); *B60W 2510/08* (2013.01); *B60W 2510/18* (2013.01); *B60W 2520/04* (2013.01); *B60W 2520/105* (2013.01); *B60W 2540/18* (2013.01); *B60W 2540/22* (2013.01); *B60W 2540/28* (2013.01); *B60W 2540/30* (2013.01); *B60W 2550/10* (2013.01); *B60W 2550/30* (2013.01); *B60W 2710/18* (2013.01); *B60W 2710/20* (2013.01); *B60W 2750/40* (2013.01); *B60W 2900/00* (2013.01); *G01S 2007/4043* (2013.01); *G01S 2007/4977* (2013.01); *G01S 2013/935* (2013.01); *G01S 2013/936* (2013.01); *G01S 2013/9325* (2013.01); *G01S 2013/9342* (2013.01); *G01S 2013/9346* (2013.01); *G01S 2013/9353* (2013.01); *G01S 2013/9357* (2013.01); *G01S 2013/9375* (2013.01); *G01S 2013/9378* (2013.01); *G01S 2013/9382* (2013.01); *G01S 2013/9385* (2013.01); *G01S 2013/9389* (2013.01); *G05D 2201/0212* (2013.01)

(58) Field of Classification Search
CPC ..... B60S 1/66; B60W 50/14; B60W 50/0098; B60W 50/02; B60W 50/0205; B60W 50/021; B60W 50/0215; B60W 50/022; B60W 50/0225; B60W 50/023; B60W 50/029; B60W 50/032; B60W 50/035; B60W 2050/0292; B60W 2050/0295; B60W 2050/0297; G02B 27/0006; G05D 1/0077

See application file for complete search history.

(56) References Cited

U.S. PATENT DOCUMENTS

| | | | |
|---|---|---|---|
| 2006/0171704 A1* | 8/2006 | Bingle | B60R 11/04 396/419 |
| 2009/0274478 A1* | 11/2009 | Kang | G03G 15/5041 399/98 |
| 2011/0242286 A1* | 10/2011 | Pace | H04N 13/296 348/47 |
| 2011/0298656 A1* | 12/2011 | Bechler | G01S 13/931 342/26 R |
| 2013/0099943 A1* | 4/2013 | Subramanya | G01S 7/2926 340/933 |
| 2013/0105264 A1* | 5/2013 | Ruth | B60L 5/26 191/59.1 |
| 2013/0245877 A1* | 9/2013 | Ferguson | B60R 1/00 701/23 |
| 2014/0232869 A1* | 8/2014 | May | H04N 7/18 348/148 |
| 2015/0009296 A1* | 1/2015 | Crona | H04N 13/0246 348/47 |
| 2015/0266489 A1* | 9/2015 | Solyom | B60W 50/029 701/23 |
| 2015/0309165 A1* | 10/2015 | Elwart | G01S 7/4026 342/61 |
| 2015/0310281 A1* | 10/2015 | Zhu | G06K 9/00805 382/104 |
| 2016/0001330 A1* | 1/2016 | Romack | B08B 3/02 134/18 |
| 2016/0170203 A1 | 6/2016 | Weigert et al. | |
| 2016/0176384 A1* | 6/2016 | Dissette | B60S 1/52 134/34 |
| 2016/0272164 A1* | 9/2016 | Hsiao | B08B 3/10 |
| 2016/0320471 A1* | 11/2016 | Preussner | G01S 13/60 |
| 2017/0059695 A1* | 3/2017 | Fetterman | G01S 7/4026 |
| 2017/0115387 A1* | 4/2017 | Luders | G01S 7/4972 |
| 2017/0210304 A1* | 7/2017 | Davies | B60S 1/52 |
| 2017/0259789 A1* | 9/2017 | McAndrew | B60S 1/528 |
| 2017/0269196 A1* | 9/2017 | Millar | G01S 7/4026 |

(56) References Cited

U.S. PATENT DOCUMENTS

| | | | |
|---|---|---|---|
| 2017/0349147 A1 | 12/2017 | Blank | |
| 2017/0369039 A1* | 12/2017 | Rousseau | B60S 1/56 |
| 2018/0009418 A1* | 1/2018 | Newman | G01S 17/936 |
| 2018/0115693 A1* | 4/2018 | Matsushima | B08B 7/02 |
| 2018/0126921 A1 | 5/2018 | Koseki | |
| 2018/0128901 A1* | 5/2018 | Pointer | G01S 7/4004 |
| 2018/0354467 A1* | 12/2018 | Glickman | B60S 1/56 |

OTHER PUBLICATIONS

Kautonen, "NextEV unveils the NIO EP9 electric supercar in London," Autoblog, 2016, retrieved from http://www.autoblog.com/2016/11/21/nextev-unveiles-the-nio-ep9-electric-supercar-in-london/, 3 pages.

White, "NextEV's NIO IP9 is an incredible four-wheel-rive electric hypercar," WIRED, 2016, retrieved from http://www.wired.co.uk/article/nextev-hypercar-nio-ep9, 6 pages.

U.S. Appl. No. 15/394,419, filed Dec. 29, 2016, Newman.

U.S. Appl. No. 15/394,402, filed Dec. 29, 2016, Newman.

International Search Report and Written Opinion for International (PCT)Patent Application No. PCT/US17/62700, dated Mar. 5, 2018, 11 pages.

Official Action for U.S. Appl. No. 15/394,419, dated Aug. 3, 2018 7 pages, Restriction Requirement.

Official Action for U.S. Appl. No. 15/394,419, dated Nov. 26, 2018 11 pages.

Final Action for U.S. Appl. No. 15/394,419, dated Apr. 25, 2019, 11 pages.

Official Action for U.S. Appl. No. 15/394,402, dated Apr. 5, 2019, 6 pages, Restriction Requirement.

International Preliminary Report on Patentability for International (PCT) Patent Application No. PCT/US17/62700, dated May 31, 2019, 10 pages.

\* cited by examiner

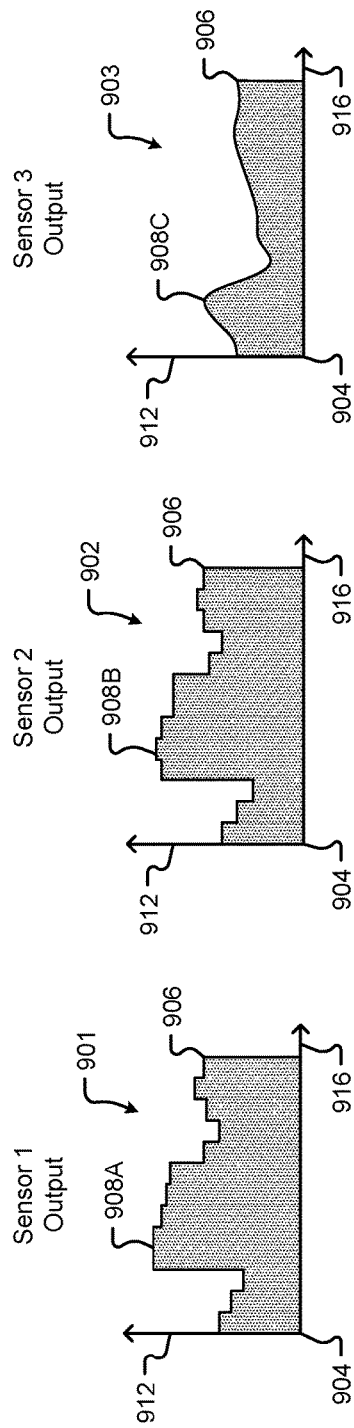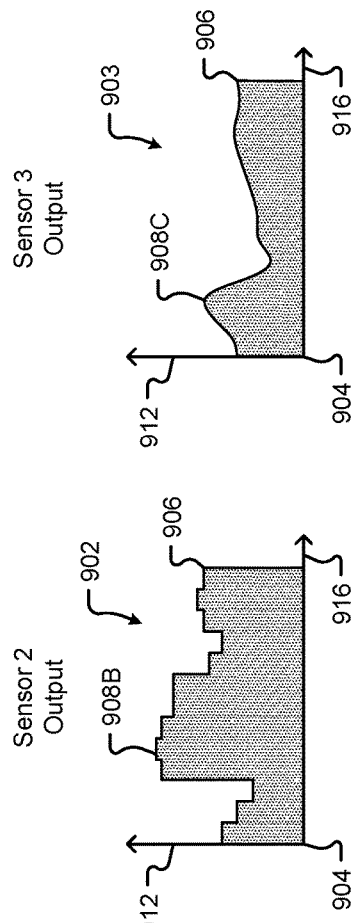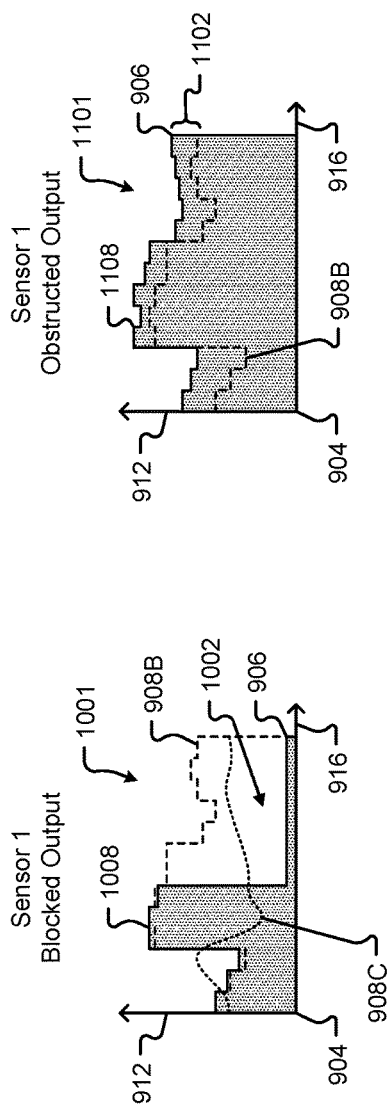

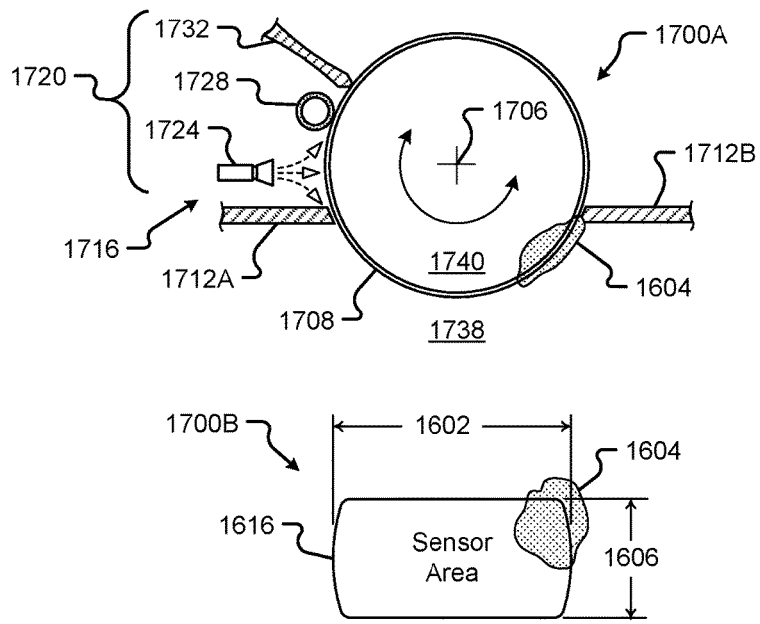
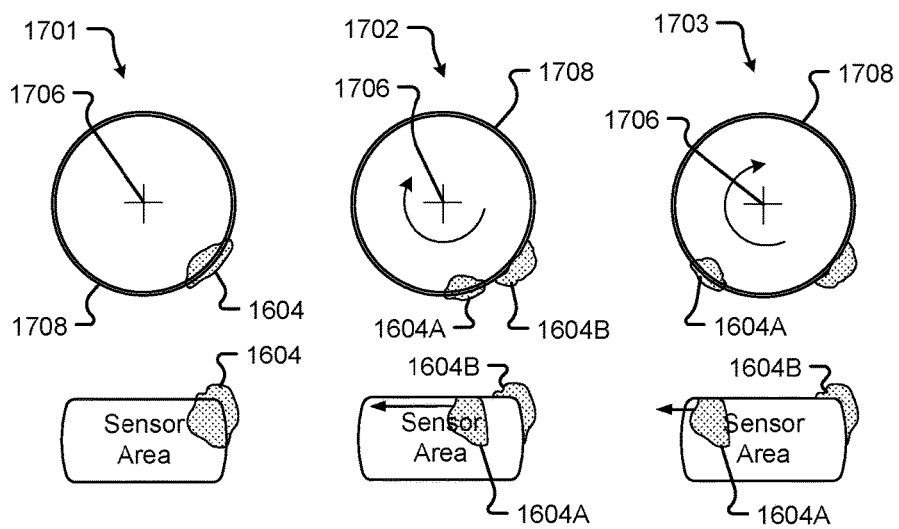
Fig. 17A
Fig. 17B    Fig. 17C    Fig. 17D

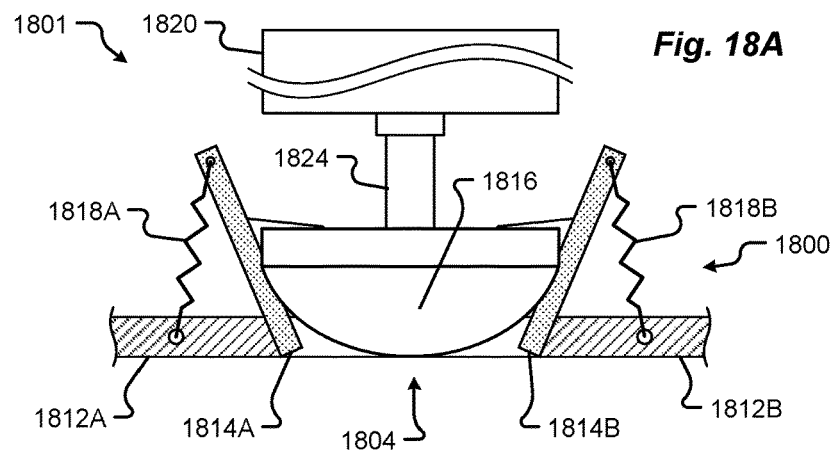
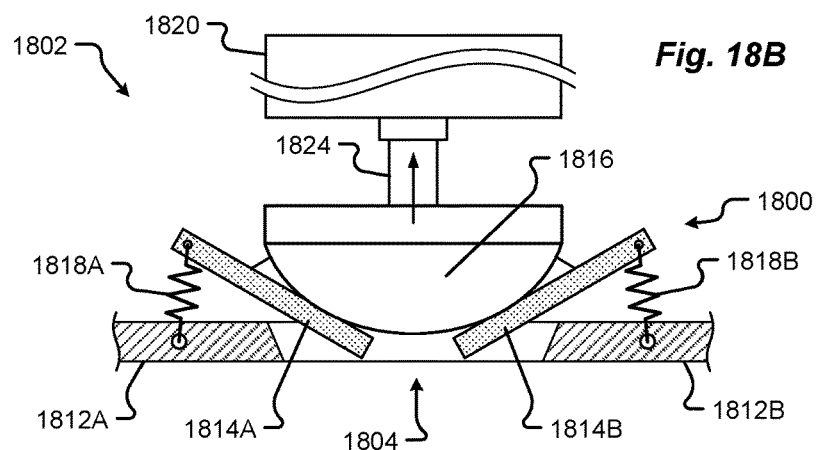
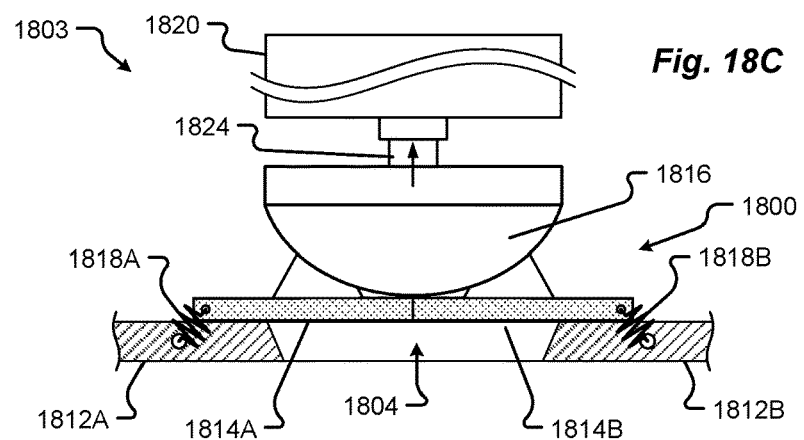

SENSOR SURFACE OBJECT DETECTION METHODS AND SYSTEMS

CROSS REFERENCE TO RELATED APPLICATIONS

The present application claims the benefits of and priority, under 35 U.S.C. § 119(e), to U.S. Provisional Application Ser. No. 62/424,976, filed on Nov. 21, 2016, entitled "Next Generation Vehicle." The entire disclosure of the application listed above is hereby incorporated by reference, in its entirety, for all that it teaches and for all purposes.

FIELD

The present disclosure is generally directed to vehicle systems, in particular, toward electric and/or hybrid-electric vehicles.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

BRIEF DESCRIPTION OF THE DRAWINGS

FIG. 9A shows a graphical representation of sensor information detected by a first sensor of the vehicle over time in accordance with embodiments of the present disclosure;

FIG. 9B shows a graphical representation of sensor information detected by a second sensor of the vehicle over time in accordance with embodiments of the present disclosure;

FIG. 9C shows a graphical representation of sensor information detected by a third sensor of the vehicle over time in accordance with embodiments of the present disclosure;

FIG. 10 shows a graphical representation of compared sensor information between sensors of the vehicle in accordance with embodiments of the present disclosure;

FIG. 11 shows a graphical representation of compared sensor information between sensors of the vehicle in accordance with embodiments of the present disclosure;

FIG. 17A shows a schematic plan and front view of components of a sensor cleaning system of the vehicle in accordance with embodiments of the present disclosure;

FIG. 17B shows a schematic plan and front view of the sensor cleaning system of FIG. 17A in a first cleaning state;

FIG. 17C shows a schematic plan and front view of the sensor cleaning system of FIG. 17A in a second cleaning state;

FIG. 17D shows a schematic plan and front view of the sensor cleaning system of FIG. 17A in a third cleaning state;

FIG. 18A shows a schematic cross-sectional view of a sensor cleaning system and sensor of the vehicle in a first cleaning state in accordance with embodiments of the present disclosure;

FIG. 18B shows a schematic cross-sectional view of a sensor cleaning system and sensor of the vehicle in a second cleaning state in accordance with embodiments of the present disclosure;

FIG. 18C shows a schematic cross-sectional view of a sensor cleaning system and sensor of the vehicle in a third cleaning state in accordance with embodiments of the present disclosure;

DETAILED DESCRIPTION

Embodiments of the present disclosure will be described in connection with a vehicle, and in some embodiments, an electric vehicle, rechargeable electric vehicle, and/or hybrid-electric vehicle and associated systems.

Figure 1:
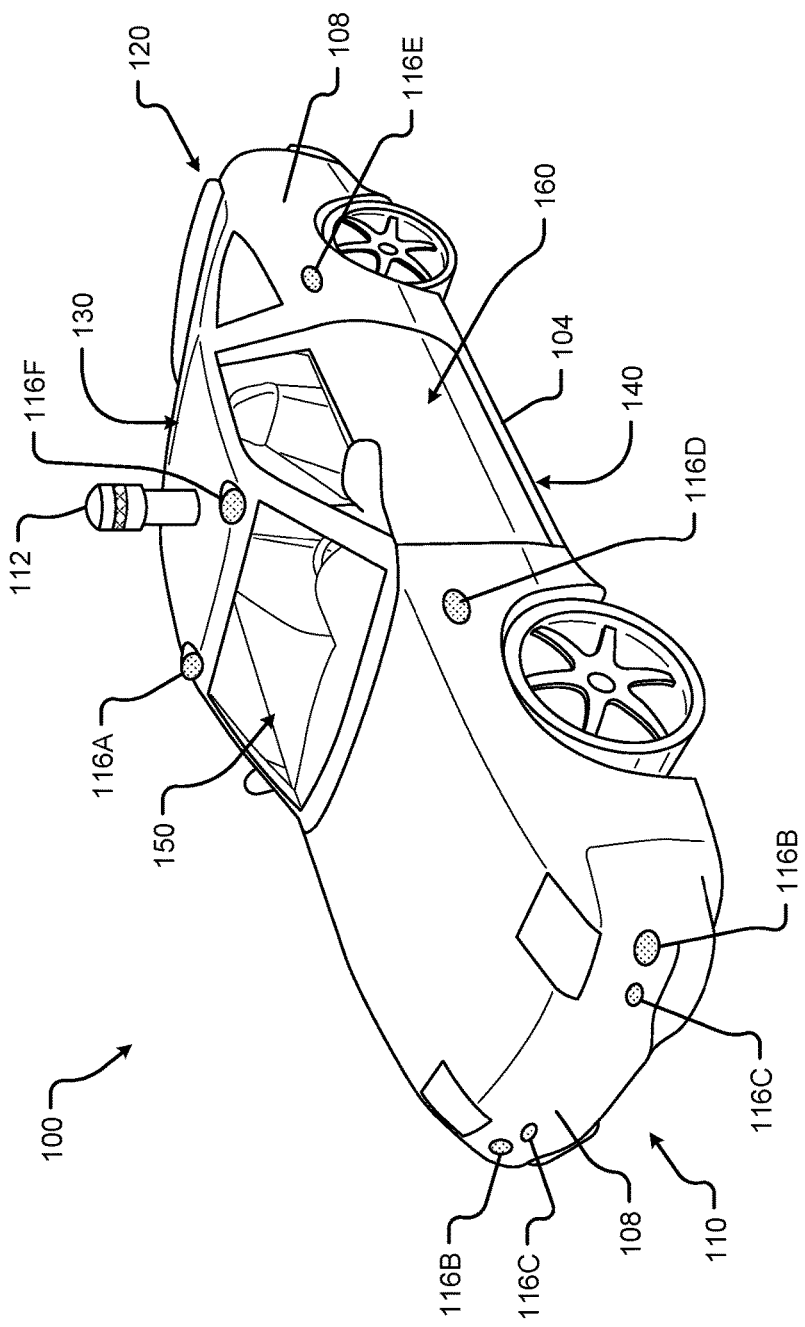
FIG. 1 shows a vehicle in accordance with embodiments of the present disclosure.

FIG. 1 shows a perspective view of a vehicle 100 in accordance with embodiments of the present disclosure. The electric vehicle 100 comprises a vehicle front 110, vehicle aft or rear 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

In some embodiments, the vehicle 100 may include a number of sensors, devices, and/or systems that are capable of assisting in driving operations. Examples of the various sensors and systems may include, but are in no way limited to, one or more of cameras (e.g., independent, stereo, combined image, etc.), infrared (IR) sensors, radio frequency (RF) sensors, ultrasonic sensors (e.g., transducers, transceivers, etc.), RADAR sensors (e.g., object-detection sensors and/or systems), LIDAR systems, odometry sensors and/or devices (e.g., encoders, etc.), orientation sensors (e.g., accelerometers, gyroscopes, magnetometer, etc.), navigation sensors and systems (e.g., GPS, etc.), and other ranging, imaging, and/or object-detecting sensors. The sensors may be disposed in an interior space 150 of the vehicle 100 and/or on an outside of the vehicle 100. In some embodiments, the sensors and systems may be disposed in one or more portions of a vehicle 100 (e.g., the frame 104, a body panel, a compartment, etc.).

The vehicle sensors and systems may be selected and/or configured to suit a level of operation associated with the vehicle 100. Among other things, the number of sensors used in a system may be altered to increase or decrease information available to a vehicle control system (e.g., affecting control capabilities of the vehicle 100). Additionally or alternatively, the sensors and systems may be part of one or more advanced driver assistance systems (ADAS) associated with a vehicle 100. In any event, the sensors and systems may be used to provide driving assistance at any level of operation (e.g., from fully-manual to fully-autonomous operations, etc.) as described herein.

The various levels of vehicle control and/or operation can be described as corresponding to a level of autonomy associated with a vehicle 100 for vehicle driving operations. For instance, at Level 0, or fully-manual driving operations, a driver (e.g., a human driver) may be responsible for all the driving control operations (e.g., steering, accelerating, braking, etc.) associated with the vehicle. Level 0 may be referred to as a "No Automation" level. At Level 1, the vehicle may be responsible for a limited number of the driving operations associated with the vehicle, while the driver is still responsible for most driving control operations. An example of a Level 1 vehicle may include a vehicle in which the throttle control and/or braking operations may be controlled by the vehicle (e.g., cruise control operations, etc.). Level 1 may be referred to as a "Driver Assistance" level. At Level 2, the vehicle may collect information (e.g., via one or more driving assistance systems, sensors, etc.) about an environment of the vehicle (e.g., surrounding area, roadway, traffic, ambient conditions, etc.) and use the collected information to control driving operations (e.g., steering, accelerating, braking, etc.) associated with the vehicle. In a Level 2 autonomous vehicle, the driver may be required to perform other aspects of driving operations not controlled by the vehicle. Level 2 may be referred to as a "Partial Automation" level. It should be appreciated that Levels 0-2 all involve the driver monitoring the driving operations of the vehicle.

At Level 3, the driver may be separated from controlling all the driving operations of the vehicle except when the vehicle makes a request for the operator to act or intervene in controlling one or more driving operations. In other words, the driver may be separated from controlling the vehicle unless the driver is required to take over for the vehicle. Level 3 may be referred to as a "Conditional Automation" level. At Level 4, the driver may be separated from controlling all the driving operations of the vehicle and the vehicle may control driving operations even when a user fails to respond to a request to intervene. Level 4 may be referred to as a "High Automation" level. At Level 5, the vehicle can control all the driving operations associated with the vehicle in all driving modes. The vehicle in Level 5 may continually monitor traffic, vehicular, roadway, and/or environmental conditions while driving the vehicle. In Level 5, there is no human driver interaction required in any driving mode. Accordingly, Level 5 may be referred to as a "Full Automation" level. It should be appreciated that in Levels 3-5 the vehicle, and/or one or more automated driving systems associated with the vehicle, monitors the driving operations of the vehicle and the driving environment.

As shown in FIG. 1, the vehicle 100 may, for example, include at least one of a ranging and imaging system 112 (e.g., LIDAR, etc.), an imaging sensor 116A, 116F (e.g., camera, IR, etc.), a radio object-detection and ranging system sensors 116B (e.g., RADAR, RF, etc.), ultrasonic sensors 116C, and/or other object-detection sensors 116D, 116E. In some embodiments, the LIDAR system 112 and/or sensors may be mounted on a roof 130 of the vehicle 100. In one embodiment, the RADAR sensors 116B may be disposed at least at a front 110, aft 120, or side 160 of the vehicle 100. Among other things, the RADAR sensors may be used to monitor and/or detect a position of other vehicles, pedestrians, and/or other objects near, or proximal to, the vehicle 100. While shown associated with one or more areas of a vehicle 100, it should be appreciated that any of the sensors and systems 116A-K, 112 illustrated in FIGS. 1 and 2 may be disposed in, on, and/or about the vehicle 100 in any position, area, and/or zone of the vehicle 100.

Figure 2:
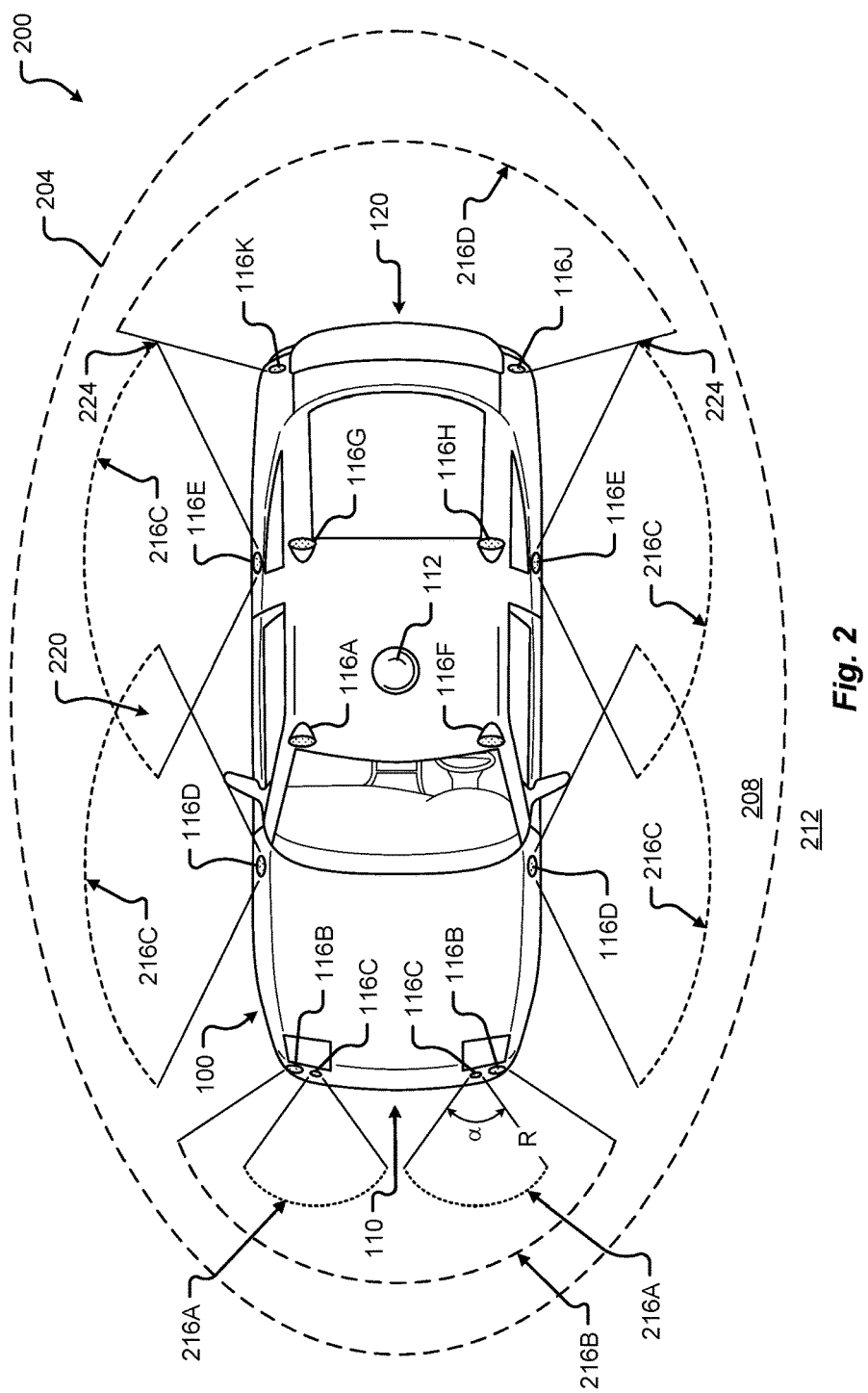
FIG. 2 shows a plan view of the vehicle in accordance with at least some embodiments of the present disclosure.

Referring now to FIG. 2, a plan view of a vehicle 100 will be described in accordance with embodiments of the present disclosure. In particular, FIG. 2 shows a vehicle sensing environment 200 at least partially defined by the sensors and systems 116A-K, 112 disposed in, on, and/or about the vehicle 100. Each sensor 116A-K may include an operational detection range R and operational detection angle α. The operational detection range R may define the effective detection limit, or distance, of the sensor 116A-K. In some cases, this effective detection limit may be defined as a distance from a portion of the sensor 116A-K (e.g., a lens, sensing surface, etc.) to a point in space offset from the sensor 116A-K. The effective detection limit may define a distance, beyond which, the sensing capabilities of the sensor 116A-K deteriorate, fail to work, or are unreliable. In some embodiments, the effective detection limit may define a distance, within which, the sensing capabilities of the sensor 116A-K are able to provide accurate and/or reliable detection information. The operational detection angle α may define at least one angle of a span, or between horizontal and/or vertical limits, of a sensor 116A-K. As can be appreciated, the operational detection limit and the operational detection angle α of a sensor 116A-K together may define the effective detection zone 216A-D (e.g., the effective detection area, and/or volume, etc.) of a sensor 116A-K.

In some embodiments, the vehicle 100 may include a ranging and imaging system 112 such as LIDAR, or the like. The ranging and imaging system 112 may be configured to detect visual information in an environment surrounding the vehicle 100. The visual information detected in the environment surrounding the ranging and imaging system 112 may be processed (e.g., via one or more sensor and/or system processors, etc.) to generate a complete 360-degree view of an environment 200 around the vehicle. The ranging and imaging system 112 may be configured to generate changing 360-degree views of the environment 200 in real-time, for instance, as the vehicle 100 drives. In some cases, the ranging and imaging system 112 may have an effective detection limit 204 that is some distance from the center of the vehicle 100 outward over 360 degrees. The effective detection limit 204 of the ranging and imaging system 112 defines a view zone 208 (e.g., an area and/or volume, etc.) surrounding the vehicle 100. Any object falling outside of the view zone 208 is in the undetected zone 212 and would not be detected by the ranging and imaging system 112 of the vehicle 100.

Sensor data and information may be collected by one or more sensors or systems 116A-K, 112 of the vehicle 100 monitoring the vehicle sensing environment 200. This information may be processed (e.g., via a processor, computer-vision system, etc.) to determine targets (e.g., objects, signs, people, markings, roadways, conditions, etc.) inside one or more detection zones 208, 216A-D associated with the vehicle sensing environment 200. In some cases, information from multiple sensors 116A-K may be processed to form composite sensor detection information. For example, a first sensor 116A and a second sensor 116F may correspond to a first camera 116A and a second camera 116F aimed in a forward traveling direction of the vehicle 100. In this example, images collected by the cameras 116A, 116F may be combined to form stereo image information. This composite information may increase the capabilities of a single sensor in the one or more sensors 116A-K by, for example, adding the ability to determine depth associated with targets in the one or more detection zones 208, 216A-D. Similar image data may be collected by rear view cameras (e.g., sensors 116G, 116H) aimed in a rearward traveling direction vehicle 100.

In some embodiments, multiple sensors 116A-K may be effectively joined to increase a sensing zone and provide increased sensing coverage. For instance, multiple RADAR sensors 116B disposed on the front 110 of the vehicle may be joined to provide a zone 216B of coverage that spans across an entirety of the front 110 of the vehicle. In some cases, the multiple RADAR sensors 116B may cover a detection zone 216B that includes one or more other sensor detection zones 216A. These overlapping detection zones may provide redundant sensing, enhanced sensing, and/or provide greater detail in sensing within a particular portion (e.g., zone 216A) of a larger zone (e.g., zone 216B). Additionally or alternatively, the sensors 116A-K of the vehicle 100 may be arranged to create a complete coverage, via one or more sensing zones 208, 216A-D around the vehicle 100. In some areas, the sensing zones 216C of two or more sensors 116D, 116E may intersect at an overlap zone 220. In some areas, the angle and/or detection limit of two or more sensing zones 216C, 216D (e.g., of two or more sensors 116E, 116J, 116K) may meet at a virtual intersection point 224.

The vehicle 100 may include a number of sensors 116E, 116G, 116H, 116J, 116K disposed proximal to the rear 120 of the vehicle 100. These sensors can include, but are in no way limited to, an imaging sensor, camera, IR, a radio object-detection and ranging sensors, RADAR, RF, ultrasonic sensors, and/or other object-detection sensors. Among other things, these sensors 116E, 116G, 116H, 116J, 116K may detect targets near or approaching the rear of the vehicle 100. For example, another vehicle approaching the rear 120 of the vehicle 100 may be detected by one or more of the ranging and imaging system (e.g., LIDAR) 112, rear-view cameras 116G, 116H, and/or rear facing RADAR sensors 116J, 116K. As described above, the images from the rear-view cameras 116G, 116H may be processed to generate a stereo view (e.g., providing depth associated with an object or environment, etc.) for targets visible to both cameras 116G, 116H. As another example, the vehicle 100 may be driving and one or more of the ranging and imaging system 112, front-facing cameras 116A, 116F, front-facing RADAR sensors 116B, and/or ultrasonic sensors 116C may detect targets in front of the vehicle 100. This approach may provide critical sensor information to a vehicle control system in at least one of the autonomous driving levels described above. For instance, when the vehicle 100 is driving autonomously (e.g., Level 3, Level 4, or Level 5) and detects other vehicles stopped in a travel path, the sensor detection information may be sent to the vehicle control system of the vehicle 100 to control a driving operation (e.g., braking, decelerating, etc.) associated with the vehicle 100 (in this example, slowing the vehicle 100 as to avoid colliding with the stopped other vehicles). As yet another example, the vehicle 100 may be operating and one or more of the ranging and imaging system 112, and/or the side-facing sensors 116D, 116E (e.g., RADAR, ultrasonic, camera, combinations thereof, and/or other type of sensor), may detect targets at a side of the vehicle 100. It should be appreciated that the sensors 116A-K may detect a target that is both at a side 160 and a front 110 of the vehicle 100 (e.g., disposed at a diagonal angle to a centerline of the vehicle 100 running from the front 110 of the vehicle 100 to the rear 120 of the vehicle). Additionally or alternatively, the sensors 116A-K may detect a target that is both, or simultaneously, at a side 160 and a rear 120 of the vehicle 100 (e.g., disposed at a diagonal angle to the centerline of the vehicle 100).

Figure 3:
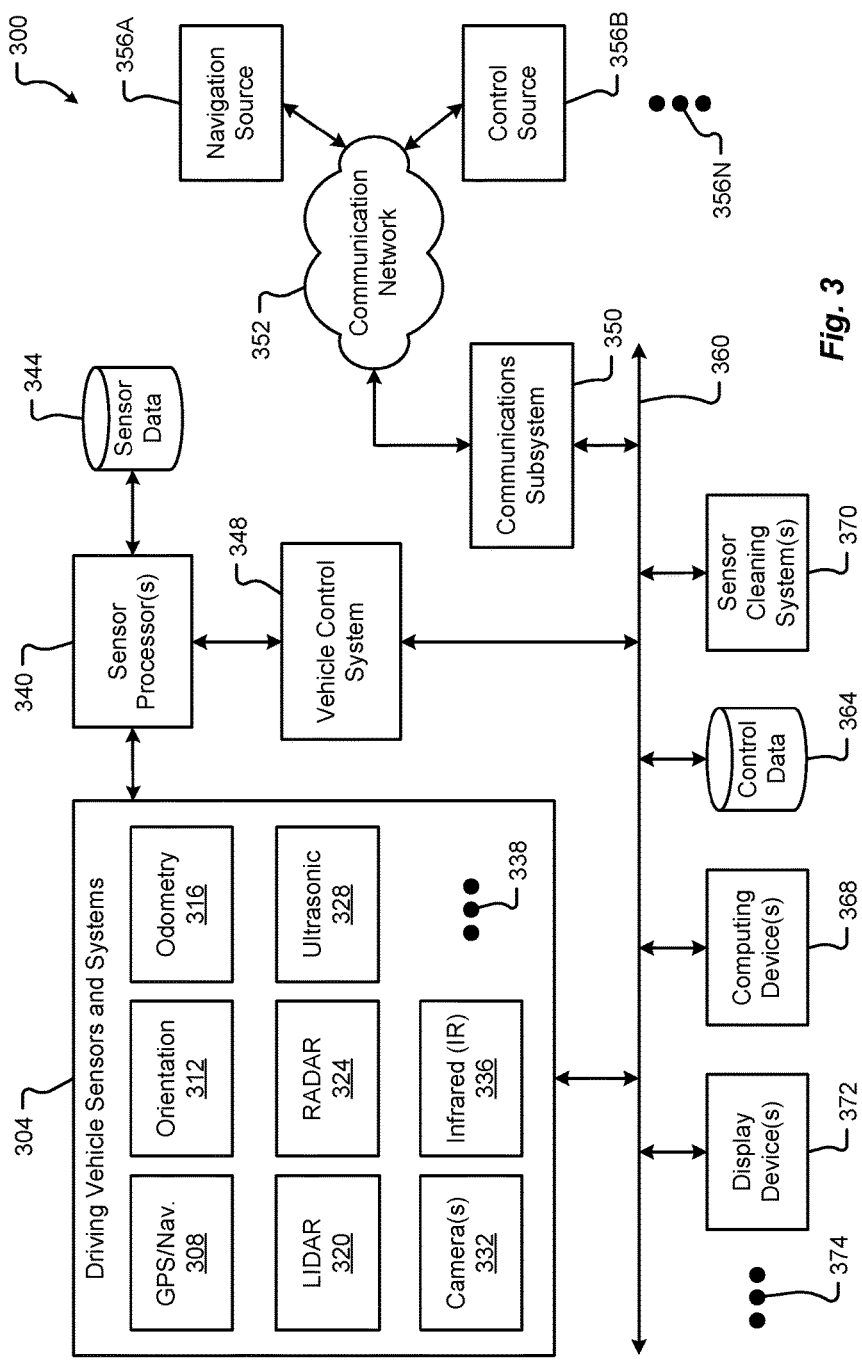
FIG. 3 is a block diagram of an embodiment of a communication environment of the vehicle in accordance with embodiments of the present disclosure.

FIG. 3 is a block diagram of an embodiment of a communication environment 300 of the vehicle 100 in accordance with embodiments of the present disclosure. The communication system 300 may include one or more vehicle driving vehicle sensors and systems 304, sensor processors 340, sensor data memory 344, vehicle control system 348, communications subsystem 350, control data 364, computing devices 368, sensor cleaning systems 370, display devices 372, and other components 374 that may be associated with a vehicle 100. These associated components may be electrically and/or communicatively coupled to one another via at least one bus 360. In some embodiments, the one or more associated components may send and/or receive signals across a communication network 352 to at least one of a navigation source 356A, a control source 356B, or some other entity 356N.

In accordance with at least some embodiments of the present disclosure, the communication network 352 may comprise any type of known communication medium or collection of communication media and may use any type of protocols, such as SIP, TCP/IP, SNA, IPX, AppleTalk, and the like, to transport messages between endpoints. The communication network 352 may include wired and/or wireless communication technologies. The Internet is an example of the communication network 352 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), such as an Ethernet network, a Token-Ring network and/or the like, a Wide Area Network (WAN), a virtual network, including without limitation a virtual private network ("VPN"); the Internet, an intranet, an extranet, a cellular network, an infra-red network; a wireless network (e.g., a network operating under any of the IEEE 802.9 suite of protocols, the Bluetooth® protocol known in the art, and/or any other wireless protocol), and any other type of packet-switched or circuit-switched network known in the art and/or any combination of these and/or other networks. In addition, it can be appreciated that the communication network 352 need not be limited to any one network type, and instead may be comprised of a number of different networks and/or network types. The communication network 352 may comprise a number of different communication media such as coaxial cable, copper cable/wire, fiber-optic cable, antennas for transmitting/receiving wireless messages, and combinations thereof.

The driving vehicle sensors and systems 304 may include at least one navigation 308 (e.g., global positioning system (GPS), etc.), orientation 312, odometry 316, LIDAR 320, RADAR 324, ultrasonic 328, camera 332, infrared (IR) 336, and/or other sensor or system 338. These driving vehicle sensors and systems 304 may be similar, if not identical, to the sensors and systems 116A-K, 112 described in conjunction with FIGS. 1 and 2.

The navigation sensor 308 may include one or more sensors having receivers and antennas that are configured to utilize a satellite-based navigation system including a network of navigation satellites capable of providing geolocation and time information to at least one component of the vehicle 100. Examples of the navigation sensor 308 as described herein may include, but are not limited to, at least one of Garmin® GLO™ family of GPS and GLONASS combination sensors, Garmin® GPS 15x™ family of sensors, Garmin® GPS 16x™ family of sensors with high-sensitivity receiver and antenna, Garmin® GPS 18x OEM family of high-sensitivity GPS sensors, Dewetron DEWE-VGPS series of GPS sensors, GlobalSat 1-Hz series of GPS sensors, other industry-equivalent navigation sensors and/or systems, and may perform navigational and/or geolocation functions using any known or future-developed standard and/or architecture.

The orientation sensor 312 may include one or more sensors configured to determine an orientation of the vehicle 100 relative to at least one reference point. In some embodiments, the orientation sensor 312 may include at least one pressure transducer, stress/strain gauge, accelerometer, gyroscope, and/or geomagnetic sensor. Examples of the navigation sensor 308 as described herein may include, but are not limited to, at least one of Bosch Sensortec BMX 160 series low-power absolute orientation sensors, Bosch Sensortec BMX055 9-axis sensors, Bosch Sensortec BMI055 6-axis inertial sensors, Bosch Sensortec BMI160 6-axis inertial sensors, Bosch Sensortec BMF055 9-axis inertial sensors (accelerometer, gyroscope, and magnetometer) with integrated Cortex M0+ microcontroller, Bosch Sensortec BMP280 absolute barometric pressure sensors, Infineon TLV493D-A1B6 3D magnetic sensors, Infineon TLI493D-W1B6 3D magnetic sensors, Infineon TL family of 3D magnetic sensors, Murata Electronics SCC2000 series combined gyro sensor and accelerometer, Murata Electronics SCC1300 series combined gyro sensor and accelerometer, other industry-equivalent orientation sensors and/or systems, and may perform orientation detection and/or determination functions using any known or future-developed standard and/or architecture.

The odometry sensor and/or system 316 may include one or more components that is configured to determine a change in position of the vehicle 100 over time. In some embodiments, the odometry system 316 may utilize data from one or more other sensors and/or systems 304 in determining a position (e.g., distance, location, etc.) of the vehicle 100 relative to a previously measured position for the vehicle 100. Additionally or alternatively, the odometry sensors 316 may include one or more encoders, Hall speed sensors, and/or other measurement sensors/devices configured to measure a wheel speed, rotation, and/or number of revolutions made over time. Examples of the odometry sensor/system 316 as described herein may include, but are not limited to, at least one of Infineon TLE4924/26/27/28C high-performance speed sensors, Infineon TL4941plusC(B) single chip differential Hall wheel-speed sensors, Infineon TL5041plusC Giant Mangnetoresistance (GMR) effect sensors, Infineon TL family of magnetic sensors, EPC Model 25SP Accu-CoderPro™ incremental shaft encoders, EPC Model 30M compact incremental encoders with advanced magnetic sensing and signal processing technology, EPC Model 925 absolute shaft encoders, EPC Model 958 absolute shaft encoders, EPC Model MA36S/MA63S/SA36S absolute shaft encoders, Dynapar™ F18 commutating optical encoder, Dynapar™ HS35R family of phased array encoder sensors, other industry-equivalent odometry sensors and/or systems, and may perform change in position detection and/or determination functions using any known or future-developed standard and/or architecture.

The LIDAR sensor/system 320 may include one or more components configured to measure distances to targets using laser illumination. In some embodiments, the LIDAR sensor/system 320 may provide 3D imaging data of an environment around the vehicle 100. The imaging data may be processed to generate a full 360-degree view of the environment around the vehicle 100. The LIDAR sensor/system 320 may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor/system 320 into a measurement environment. The rotating reflective surface may be configured to continually rotate 360 degrees about an axis, such that the plurality of laser beams is directed in a full 360-degree range around the vehicle 100. A photodiode receiver of the LIDAR sensor/system 320 may detect when light from the plurality of laser beams emitted into the measurement environment returns (e.g., reflected echo) to the LIDAR sensor/system 320. The LIDAR sensor/system 320 may calculate, based on a time associated with the emission of light to the detected return of light, a distance from the vehicle 100 to the illuminated target. In some embodiments, the LIDAR sensor/system 320 may generate over 2.0 million points per second and have an effective operational range of at least 100 meters. Examples of the LIDAR sensor/system 320 as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus: Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the vehicle 100 using any known or future-developed standard and/or architecture.

The RADAR sensors 324 may include one or more radio components that are configured to detect objects/targets in an environment of the vehicle 100. In some embodiments, the RADAR sensors 324 may determine a distance, position, and/or movement vector (e.g., angle, speed, etc.) associated with a target over time. The RADAR sensors 324 may include a transmitter configured to generate and emit electromagnetic waves (e.g., radio, microwaves, etc.) and a receiver configured to detect returned electromagnetic waves. In some embodiments, the RADAR sensors 324 may include at least one processor configured to interpret the returned electromagnetic waves and determine locational properties of targets. Examples of the RADAR sensors 324 as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the vehicle 100 using any known or future-developed standard and/or architecture.

The ultrasonic sensors 328 may include one or more components that are configured to detect objects/targets in an environment of the vehicle 100. In some embodiments, the ultrasonic sensors 328 may determine a distance, position, and/or movement vector (e.g., angle, speed, etc.) associated with a target over time. The ultrasonic sensors 328 may include an ultrasonic transmitter and receiver, or transceiver, configured to generate and emit ultrasound waves and interpret returned echoes of those waves. In some embodiments, the ultrasonic sensors 328 may include at least one processor configured to interpret the returned ultrasonic waves and determine locational properties of targets. Examples of the ultrasonic sensors 328 as described herein may include, but are not limited to, at least one of Texas Instruments TIDA-00151 automotive ultrasonic sensor interface IC sensors, MaxBotix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the vehicle 100 using any known or future-developed standard and/or architecture.

The camera sensors 332 may include one or more components configured to detect image information associated with an environment of the vehicle 100. In some embodiments, the camera sensors 332 may include a lens, filter, image sensor, and/or a digital image processor. It is an aspect of the present disclosure that multiple camera sensors 332 may be used together to generate stereo images providing depth measurements. Examples of the camera sensors 332 as described herein may include, but are not limited to, at least one of ON Semiconductor® MT9V024 Global Shutter VGA GS CMOS image sensors, Teledyne DALSA Falcon2 camera sensors, CMOSIS CMV50000 high-speed CMOS image sensors, other industry-equivalent camera sensors and/or systems, and may perform visual target and/or obstacle detection in an environment around the vehicle 100 using any known or future-developed standard and/or architecture.

The infrared (IR) sensors 336 may include one or more components configured to detect image information associated with an environment of the vehicle 100. The IR sensors 336 may be configured to detect targets in low-light, dark, or poorly-lit environments. The IR sensors 336 may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors 336 may include at least one processor configured to interpret the returned IR light and determine locational properties of targets. The IR sensors 336 may be configured to detect and/or measure a temperature associated with a target (e.g., an object, pedestrian, other vehicle, etc.). Examples of IR sensors 336 as described herein may include, but are not limited to, at least one of Opto Diode lead-salt IR array sensors, Opto Diode OD-850 Near-IR LED sensors, Opto Diode SA/SHA727 steady state IR emitters and IR detectors, FLIR® LS microbolometer sensors, FLIR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the vehicle 100 using any known or future-developed standard and/or architecture.

In some embodiments, the driving vehicle sensors and systems 304 may include other sensors 338 and/or combinations of the sensors 308-336 described above. Additionally or alternatively, one or more of the sensors 308-336 described above may include one or more processors configured to process and/or interpret signals detected by the one or more sensors 308-336. In some embodiments, the processing of at least some sensor information provided by the vehicle sensors and systems 304 may be processed by at least one sensor processor 340. Raw and/or processed sensor data may be stored in a sensor data memory 344 storage medium. In some embodiments, the sensor data memory 344 may store instructions used by the sensor processor 340 for processing sensor information provided by the sensors and systems 304. In any event, the sensor data memory 344 may be a disk drive, optical storage device, solid-state storage device such as a random access memory ("RAM") and/or a read-only memory ("ROM"), which can be programmable, flash-updateable, and/or the like.

The vehicle control system 348 may receive processed sensor information from the sensor processor 340 and determine to control an aspect of the vehicle 100. Controlling an aspect of the vehicle 100 may include presenting information via one or more display devices 372 associated with the vehicle, sending commands to one or more computing devices 368 associated with the vehicle, and/or controlling a driving operation of the vehicle. In some embodiments, the vehicle control system 348 may correspond to one or more computing systems that control driving operations of the vehicle 100 in accordance with the Levels of driving autonomy described above. In one embodiment, the vehicle control system 348 may operate a speed of the vehicle 100 by controlling an output signal to the accelerator and/or braking system of the vehicle. In this example, the vehicle control system 348 may receive sensor data describing an environment surrounding the vehicle 100 and, based on the sensor data received, determine to adjust the acceleration, power output, and/or braking of the vehicle 100. The vehicle control system 348 may additionally control steering and/or other driving functions of the vehicle 100.

The vehicle control system 348 may communicate, in real-time, with the driving sensors and systems 304 forming a feedback loop. In particular, upon receiving sensor information describing a condition of targets in the environment surrounding the vehicle 100, the vehicle control system 348 may autonomously make changes to a driving operation of the vehicle 100. The vehicle control system 348 may then receive subsequent sensor information describing any change to the condition of the targets detected in the environment as a result of the changes made to the driving operation. This continual cycle of observation (e.g., via the sensors, etc.) and action (e.g., selected control or non-control of vehicle operations, etc.) allows the vehicle 100 to operate autonomously in the environment.

In some embodiments, the one or more components of the vehicle 100 (e.g., the driving vehicle sensors 304, vehicle control system 348, display devices 372, etc.) may communicate across the communication network 352 to one or more entities 356A-N via a communications subsystem 350 of the vehicle 100. Embodiments of the communications subsystem 350 are described in greater detail in conjunction with FIG. 5. For instance, the navigation sensors 308 may receive global positioning, location, and/or navigational information from a navigation source 356A. In some embodiments, the navigation source 356A may be a global navigation satellite system (GNSS) similar, if not identical, to NAVSTAR GPS, GLONASS, EU Galileo, and/or the BeiDou Navigation Satellite System (BDS) to name a few.

In some embodiments, the vehicle control system 348 may receive control information from one or more control sources 356B. The control source 356 may provide vehicle control information including autonomous driving control commands, vehicle operation override control commands, and the like. The control source 356 may correspond to an autonomous vehicle control system, a traffic control system, an administrative control entity, and/or some other controlling server. It is an aspect of the present disclosure that the vehicle control system 348 and/or other components of the vehicle 100 may exchange communications with the control source 356 across the communication network 352 and via the communications subsystem 350.

Information associated with controlling driving operations of the vehicle 100 may be stored in a control data memory 364 storage medium. The control data memory 364 may store instructions used by the vehicle control system 348 for controlling driving operations of the vehicle 100, historical control information, autonomous driving control rules, and the like. In some embodiments, the control data memory 364 may be a disk drive, optical storage device, solid-state storage device such as a random access memory ("RAM") and/or a read-only memory ("ROM"), which can be programmable, flash-updateable, and/or the like.

The sensor cleaning systems 370 may include any device and/or system that is configured to clean a sensor (e.g., the driving vehicle sensors and systems 304, ranging and imaging system 112, sensors 116A-K, etc., and/or combinations thereof) of the vehicle 100. In some embodiments, the sensor cleaning systems 370 may be described in conjunction with FIGS. 16A-19C. Additionally or alternatively, the sensor cleaning systems 370 may receive a command or instruction from the sensor processors 340, the vehicle control system 348, etc. to initiate a cleaning operation for one or more of the sensors. The cleaning operation may be initiated in response to the sensor processors 340 and/or vehicle control system 348 detecting that at least one sensor of the vehicle 100 is blocked, obscured, obstructed, and/or failing over time. In some embodiments, the sensor cleaning system 370 may include a processor and memory, or a controller, configured to communicate with one or more components of the vehicle 100. The sensor cleaning system may include one or more cleaning devices associated with various sensors of the vehicle 100. It is an aspect of the present disclosure that objects on sensor surfaces may be detected in accordance with one or more of the methods 1400, 1500 disclosed in conjunction with FIGS. 14 and 15.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

Figure 4:
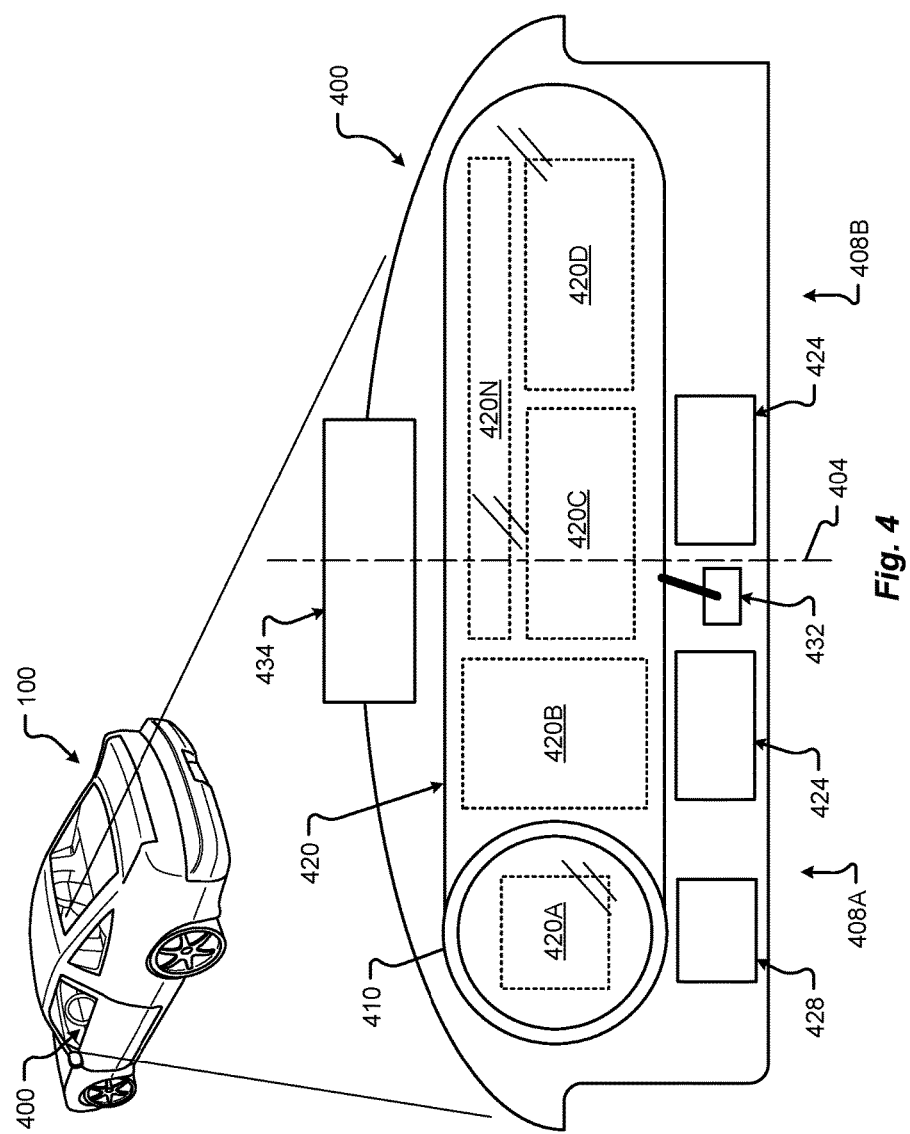
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
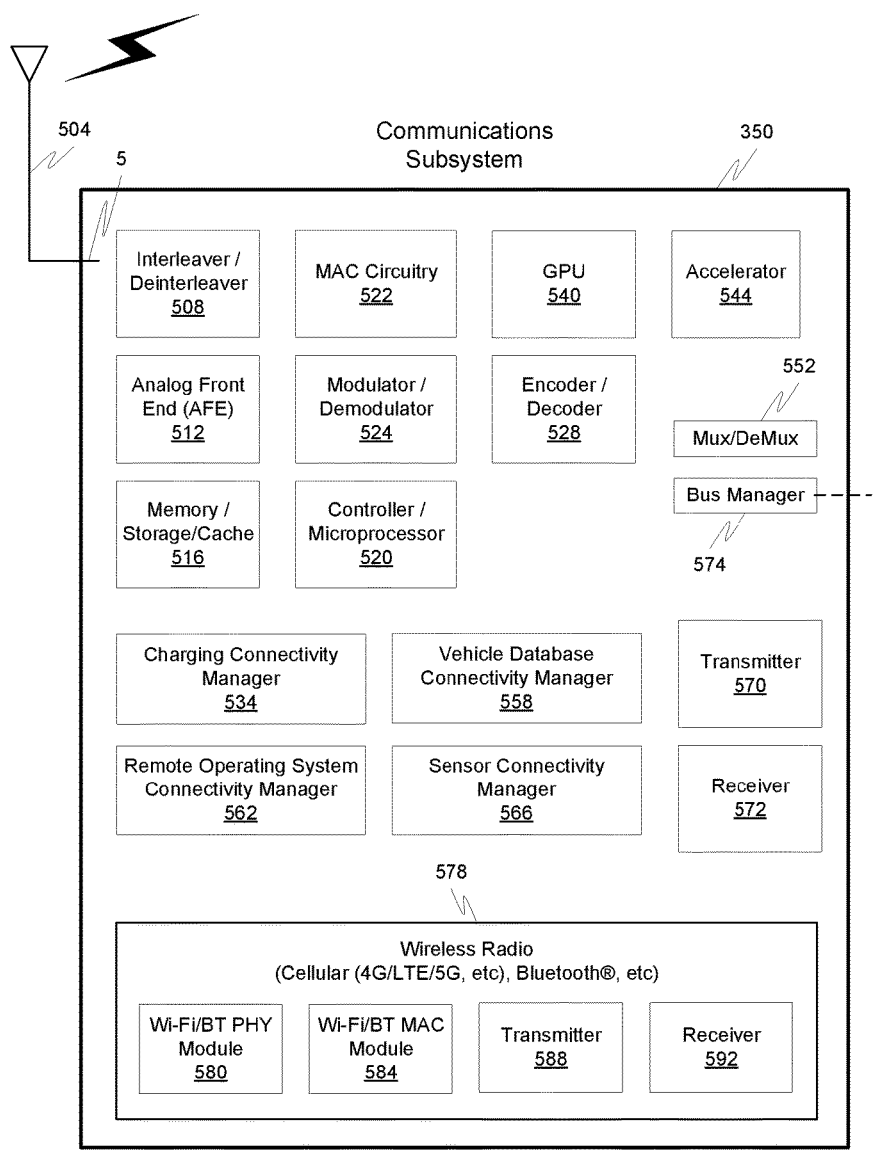
FIG. 5 is a block diagram of an embodiment of a communications subsystem of the vehicle.

FIG. 5 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with other vehicle(s).

The communications subsystem 350 can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem 350 can include one or more communications links (that can be wired or wireless) and/or communications busses (managed by the bus manager 574), including one or more of CANbus, OBD-II, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), and the like or in general any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem 350 enables communications between any if the inter-vehicle systems and subsystems as well as communications with non-collocated resources, such as those reachable over a network such as the Internet.

The communications subsystem 350, in addition to well-known componentry (which has been omitted for clarity), includes interconnected elements including one or more of: one or more antennas 504, an interleaver/deinterleaver 508, an analog front end (AFE) 512, memory/storage/cache 516, controller/microprocessor 520, MAC circuitry 522, modulator/demodulator 524, encoder/decoder 528, a plurality of connectivity managers 534, 558, 562, 566, GPU 540, accelerator 544, a multiplexer/demultiplexer 552, transmitter 570, receiver 572 and wireless radio 578 components such as a Wi-Fi PHY/Bluetooth® module 580, a Wi-Fi/BT MAC module 584, transmitter 588 and receiver 592. The various elements in the device 350 are connected by one or more links/busses 5 (not shown, again for sake of clarity).

The device 350 can have one more antennas 504, for use in wireless communications such as multi-input multi-output (MIMO) communications, multi-user multi-input multi-output (MU-MIMO) communications Bluetooth®, LTE, 4G, 5G, Near-Field Communication (NFC), etc., and in general for any type of wireless communications. The antenna(s) 504 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle 100 and/or in another vehicle.

Antenna(s) 504 generally interact with the Analog Front End (AFE) 512, which is needed to enable the correct processing of the received modulated signal and signal conditioning for a transmitted signal. The AFE 512 can be functionally located between the antenna and a digital baseband system in order to convert the analog signal into a digital signal for processing and vice-versa.

The subsystem 350 can also include a controller/microprocessor 520 and a memory/storage/cache 516. The subsystem 350 can interact with the memory/storage/cache 516 which may store information and operations necessary for configuring and transmitting or receiving the information described herein. The memory/storage/cache 516 may also be used in connection with the execution of application programming or instructions by the controller/microprocessor 520, and for temporary or long term storage of program instructions and/or data. As examples, the memory/storage/cache 520 may comprise a computer-readable device, RAM, ROM, DRAM, SDRAM, and/or other storage device(s) and media.

The controller/microprocessor 520 may comprise a general purpose programmable processor or controller for executing application programming or instructions related to the subsystem 350. Furthermore, the controller/microprocessor 520 can perform operations for configuring and transmitting/receiving information as described herein. The controller/microprocessor 520 may include multiple processor cores, and/or implement multiple virtual processors. Optionally, the controller/microprocessor 520 may include multiple physical processors. By way of example, the controller/microprocessor 520 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 350 can further include a transmitter 570 and receiver 572 which can transmit and receive signals, respectively, to and from other devices, subsystems and/or other destinations using the one or more antennas 504 and/or links/busses. Included in the subsystem 350 circuitry is the medium access control or MAC Circuitry 522. MAC circuitry 522 provides for controlling access to the wireless medium. In an exemplary embodiment, the MAC circuitry 522 may be arranged to contend for the wireless medium and configure frames or packets for communicating over the wired/wireless medium.

The subsystem 350 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by Wi-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 350 also includes a GPU 540, an accelerator 544, a Wi-Fi/BT/BLE PHY module 580 and a Wi-Fi/BT/BLE MAC module 584 and wireless transmitter 588 and receiver 592. In some embodiments, the GPU 540 may be a graphics processing unit, or visual processing unit, comprising at least one circuit and/or chip that manipulates and changes memory to accelerate the creation of images in a frame buffer for output to at least one display device. The GPU 540 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 534, 558, 562, 566 manage and/or coordinate communications between the subsystem 350 and one or more of the systems disclosed herein and one or more other devices/systems. The connectivity managers 534, 558, 562, 566 include a charging connectivity manager 534, a vehicle database connectivity manager 558, a remote operating system connectivity manager 562, and a sensor connectivity manager 566.

The charging connectivity manager 534 can coordinate not only the physical connectivity between the vehicle 100 and a charging device/vehicle, but can also communicate with one or more of a power management controller, one or more third parties and optionally a billing system(s). As an example, the vehicle 100 can establish communications with the charging device/vehicle to one or more of coordinate interconnectivity between the two (e.g., by spatially aligning the charging receptacle on the vehicle with the charger on the charging vehicle) and optionally share navigation information. Once charging is complete, the amount of charge provided can be tracked and optionally forwarded to, for example, a third party for billing. In addition to being able to manage connectivity for the exchange of power, the charging connectivity manager 534 can also communicate information, such as billing information to the charging vehicle and/or a third party. This billing information could be, for example, the owner of the vehicle, the driver/occupant(s) of the vehicle, company information, or in general any information usable to charge the appropriate entity for the power received.

The vehicle database connectivity manager 558 allows the subsystem to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general any information stored in the vehicle database can optionally be shared with any one or more other devices optionally subject to any privacy or confidentially restrictions.

The remote operating system connectivity manager 562 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 566 facilitates communications between any one or more of the vehicle sensors (e.g., the driving vehicle sensors and systems 304, etc.) and any one or more of the other vehicle systems. The sensor connectivity manager 566 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (internet protocol) address(es), associated with the vehicle and one or other system or subsystems or components therein. These identifiers can be used in conjunction with any one or more of the connectivity managers as discussed herein.

Figure 6:
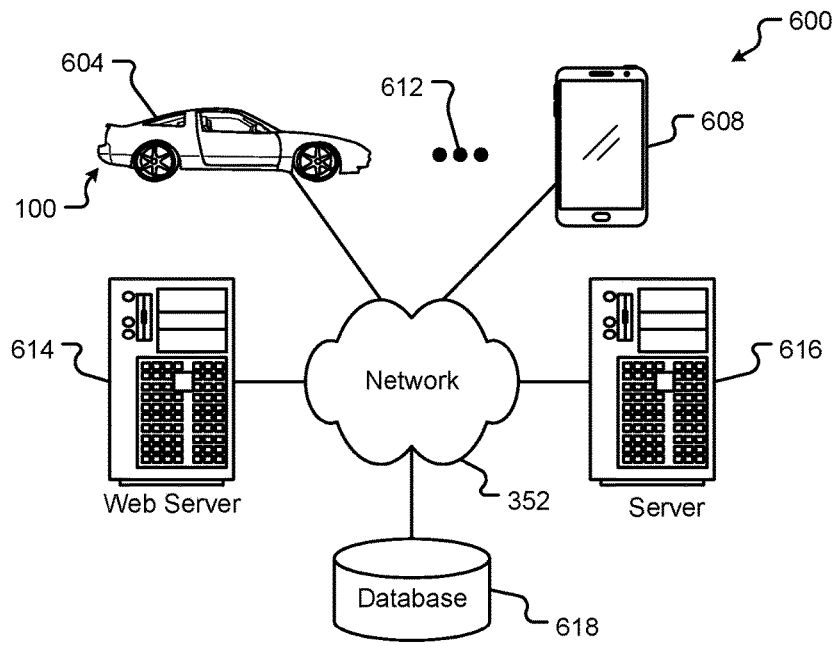
FIG. 6 is a block diagram of a computing environment associated with the embodiments presented herein.

FIG. 6 illustrates a block diagram of a computing environment 600 that may function as the servers, user computers, or other systems provided and described herein. The computing environment 600 includes one or more user computers, or computing devices, such as a vehicle computing device 604, a communication device 608, and/or more 612. The computing devices 604, 608, 612 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 604, 608, 612 may also have any of a variety of applications, including for example, database client and/or server applications, and web browser applications. Alternatively, the computing devices 604, 608, 612 may be any other electronic device, such as a thin-client computer, Internet-enabled mobile telephone, and/or personal digital assistant, capable of communicating via a network 352 and/or displaying and navigating web pages or other types of electronic documents. Although the exemplary computing environment 600 is shown with two computing devices, any number of user computers or computing devices may be supported.

The computing environment 600 may also include one or more servers 614, 616. In this example, server 614 is shown as a web server and server 616 is shown as an application server. The web server 614, which may be used to process requests for web pages or other electronic documents from computing devices 604, 608, 612. The web server 614 can be running an operating system including any of those discussed above, as well as any commercially-available server operating systems. The web server 614 can also run a variety of server applications, including SIP (Session Initiation Protocol) servers, HTTP(s) servers, FTP servers, CGI servers, database servers, Java servers, and the like. In some instances, the web server 614 may publish operations available operations as one or more web services.

The computing environment 600 may also include one or more file and or/application servers 616, which can, in addition to an operating system, include one or more applications accessible by a client running on one or more of the computing devices 604, 608, 612. The server(s) 616 and/or 614 may be one or more general purpose computers capable of executing programs or scripts in response to the computing devices 604, 608, 612. As one example, the server 616, 614 may execute one or more web applications. The web application may be implemented as one or more scripts or programs written in any programming language, such as Java™, C, C#®, or C++, and/or any scripting language, such as Perl, Python, or TCL, as well as combinations of any programming/scripting languages. The application server(s) 616 may also include database servers, including without limitation those commercially available from Oracle®, Microsoft®, Sybase®, IBM® and the like, which can process requests from database clients running on a computing device 604, 608, 612.

The web pages created by the server 614 and/or 616 may be forwarded to a computing device 604, 608, 612 via a web (file) server 614, 616. Similarly, the web server 614 may be able to receive web page requests, web services invocations, and/or input data from a computing device 604, 608, 612 (e.g., a user computer, etc.) and can forward the web page requests and/or input data to the web (application) server 616. In further embodiments, the server 616 may function as a file server. Although for ease of description, FIG. 6 illustrates a separate web server 614 and file/application server 616, those skilled in the art will recognize that the functions described with respect to servers 614, 616 may be performed by a single server and/or a plurality of specialized servers, depending on implementation-specific needs and parameters. The computer systems 604, 608, 612, web (file) server 614 and/or web (application) server 616 may function as the system, devices, or components described in FIGS. 1-6.

The computing environment 600 may also include a database 618. The database 618 may reside in a variety of locations. By way of example, database 618 may reside on a storage medium local to (and/or resident in) one or more of the computers 604, 608, 612, 614, 616. Alternatively, it may be remote from any or all of the computers 604, 608, 612, 614, 616, and in communication (e.g., via the network 352) with one or more of these. The database 618 may reside in a storage-area network ("SAN") familiar to those skilled in the art. Similarly, any necessary files for performing the functions attributed to the computers 604, 608, 612, 614, 616 may be stored locally on the respective computer and/or remotely, as appropriate. The database 618 may be a relational database, such as Oracle 20i®, that is adapted to store, update, and retrieve data in response to SQL-formatted commands.

Figure 7:
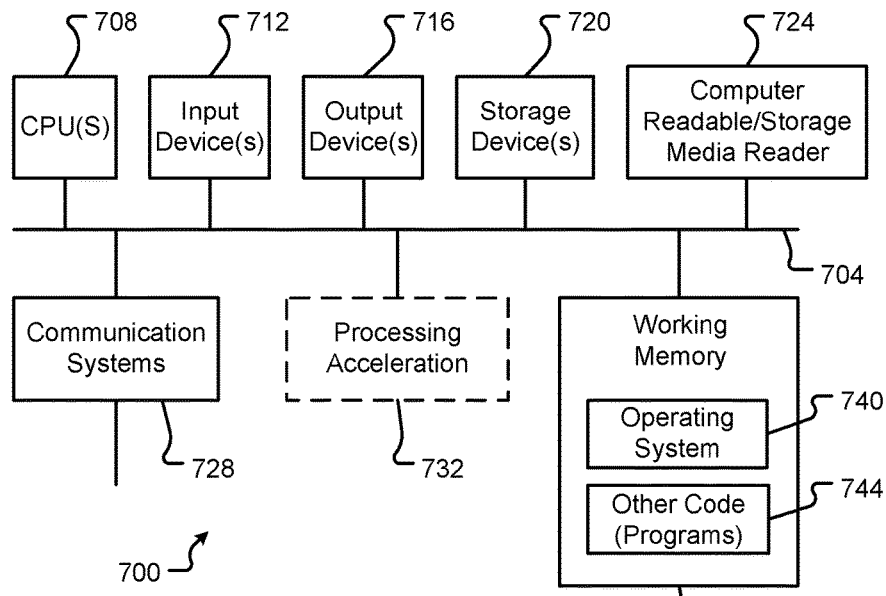
FIG. 7 is a block diagram of a computing device associated with one or more components described herein.

FIG. 7 illustrates one embodiment of a computer system 700 upon which the servers, user computers, computing devices, or other systems or components described above may be deployed or executed. The computer system 700 is shown comprising hardware elements that may be electrically coupled via a bus 704. The hardware elements may include one or more central processing units (CPUs) 708; one or more input devices 712 (e.g., a mouse, a keyboard, etc.); and one or more output devices 716 (e.g., a display device, a printer, etc.). The computer system 700 may also include one or more storage devices 720. By way of example, storage device(s) 720 may be disk drives, optical storage devices, solid-state storage devices such as a random access memory ("RAM") and/or a read-only memory ("ROM"), which can be programmable, flash-updateable and/or the like.

The computer system 700 may additionally include a computer-readable storage media reader 724; a communications system 728 (e.g., a modem, a network card (wireless or wired), an infra-red communication device, etc.); and working memory 736, which may include RAM and ROM devices as described above. The computer system 700 may also include a processing acceleration unit 732, which can include a DSP, a special-purpose processor, and/or the like.

The computer-readable storage media reader 724 can further be connected to a computer-readable storage medium, together (and, optionally, in combination with storage device(s) 720) comprehensively representing remote, local, fixed, and/or removable storage devices plus storage media for temporarily and/or more permanently containing computer-readable information. The communications system 728 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 700 may also comprise software elements, shown as being currently located within a working memory 736, including an operating system 740 and/or other code 744. It should be appreciated that alternate embodiments of a computer system 700 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 340, 708 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

Figure 8A:
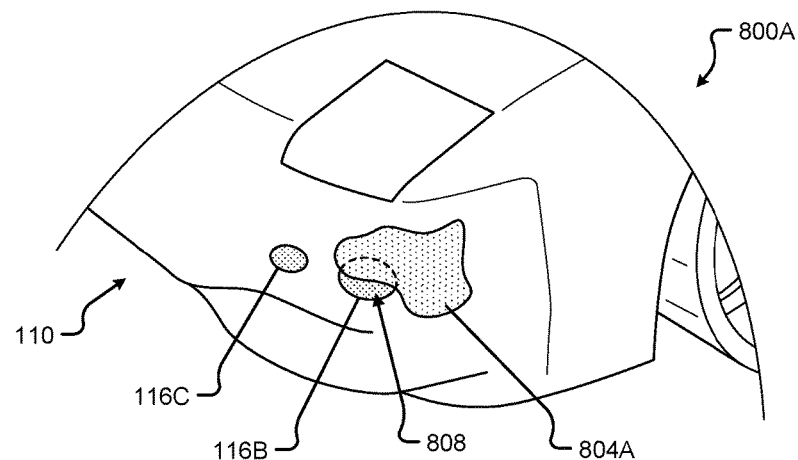
FIG. 8A shows an obstructed sensor associated with a portion of the vehicle in accordance with embodiments of the present disclosure.
Figure 8B:
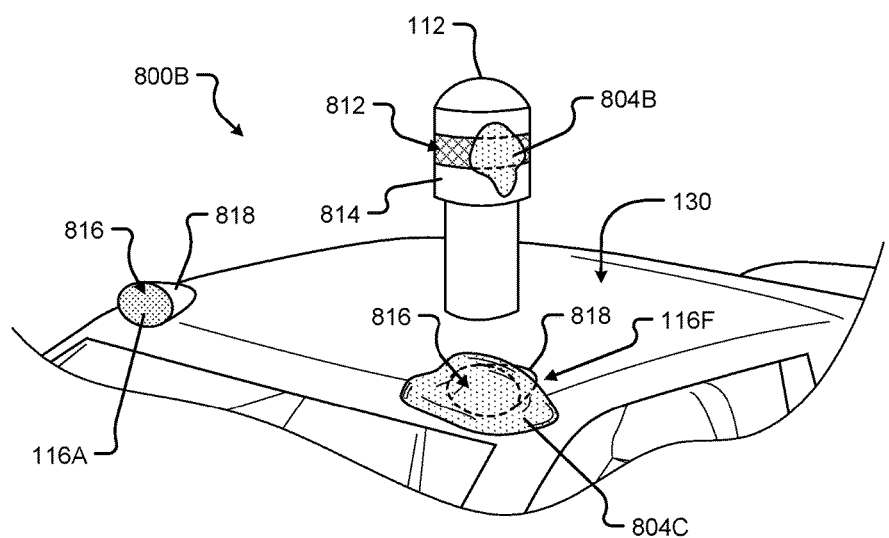
FIG. 8B shows multiple obstructed sensors associated with a portion of the vehicle in accordance with embodiments of the present disclosure.

FIGS. 8A and 8B show various sensors 112, 116A, 116B, 116F associated with portions of the vehicle 100 (e.g., the front 110 and roof 130 of the vehicle 100, etc.) having at least partial obstructions. The obstruction and/or blockage may be associated with an object that is attached to and/or in contact with a surface of the sensor. This object may be in the form of a fluid, a solid, a vapor, etc., and/or combinations thereof. Examples of objects may include, but are in no way limited to, blood, chemicals, debris, detritus, dirt, dust, food, frost, hail, ice, insects, mud, paint, projectiles, rubbish, sleet, snow, tar, trash, etc., damaged surfaces caused by projectiles and/or collisions (e.g., scratches, chips, dents, etc.), and/or combinations thereof. In some embodiments, the object may partially and/or fully obstruct a sensing capability (e.g., viewing, detecting, ranging, imaging, etc.) of a sensor or a group of sensors (e.g., linked sensors, combined detection sensors, etc.). In some embodiments, sensors may be grouped together by the sensor processor 340 and an output from the group of sensors may be used to generate a composite sensor output over time for the group of sensors.

Referring to FIG. 8A, a front 110 of a vehicle 100 is shown with a sensor 116B that is at least partially obstructed by an object 804A. As shown in FIG. 8A, the first vehicle portion 800A of the vehicle 100 may include a number of sensors 116B, 116C. In some embodiments, these sensors 116B, 116C may correspond to the radio object-detection and ranging system sensors 116B (e.g., RADAR, RF, etc.), and ultrasonic sensors 116C as described in conjunction with FIGS. 1 and 2. While the object is shown on the radio object-detection and ranging system sensor 116B in FIG. 8A, it should be appreciated that a sensor-obstruction object may be on any of the sensors described herein and are not limited to the examples shown. The object 804A of FIG. 8A is shown obstructing an upper portion of the sensor surface 808 of the sensor 116B. In one embodiment, this type of partial sensor obstruction (e.g., object 804B) may be associated with, for example, mud or snow on the sensor surface 808.

FIG. 8B shows a top or roof 130 of a vehicle 100 with multiple obstructed sensors 112, 116F. In some embodiments, one or more of the sensors (e.g., ranging and imaging system 112, imaging sensor 116F, etc.) associated with a vehicle 100 may be obstructed at some level, while other sensors (e.g., imaging sensor 116A) may be unobstructed. The second vehicle portion 800B shows a sensor surface (e.g., a lens, cover, protective shield, etc.) of the ranging and imaging system 112 (e.g., LIDAR sensor/system 112, 320) is at least partially obstructed by an object 804B. As shown in FIG. 8B, the object 804B overlaps a portion of the body 814, or housing, and the sensor surface 812 of the ranging and imaging system 112. In one embodiment, this type of partial sensor obstruction (e.g., object 804B) may be associated with, for instance, detritus (e.g., bird droppings, tree sap, etc.) on the sensor surface 812.

In some embodiments, an object 804C may completely obstruct and/or block a sensor (e.g., imaging sensor 116F) of the vehicle 100. For example, FIG. 8B shows an imaging sensor 116F (e.g., a camera, IR sensor, etc.) with a completely obstructed sensor surface 816. In some embodiments, the object 804C may cover an entirety of the sensor 116F and/or the sensor body 818. In one embodiment, this type of complete sensor surface 816 obstruction (e.g., object 804C) may be associated with, for instance, snow, ice, hail, or rubbish (e.g., plastic bag, paper, etc.) covering the sensor surface 816.

FIGS. 9A-9C show graphical representations 901-903 of detected sensor information over time by different sensors (e.g., first, second, and third sensors, etc.) of the vehicle 100. As provided herein, the term sensors may be used to refer to any of the sensors (e.g., the driving vehicle sensors and systems 304, ranging and imaging system 112, sensors 116A-K, etc.), or combinations of sensors, of the vehicle 100. As shown in FIGS. 9A-9C, each graphical representation 901-903 includes a chart having an origin 904 (or first detection point), an end 906 (or last detection point), an output (or number of outputs) over time 908A-C (e.g., waveform), a vertical axis 912 representing an intensity associated with detected sensor information, and a horizontal axis 916 representing the time associated with each output.

The first detection point 904 may correspond to a point in time when the sensor began detecting (e.g., providing detection information, etc.). In some cases, the first detection point 904 may correspond to a first point of an analyzed portion of detected sensor information. In this example, the first detection point 904 may not be the point in time when the sensor began detecting, but may be a point defined or automatically selected by the sensor processors 340 in determining a capability of the sensor for measuring an environment of the vehicle 100.

The last detection point 906 may correspond to a point in time when the sensor stopped detecting (e.g., ceasing to provide detection information). In some cases, the last detection point 906 may correspond to a final point of an analyzed portion of detected sensor information. In this example, the last detection point 906 may not be the point in time when the sensor stopped detecting, but may be a final point defined or automatically selected by the sensor processors 340 in determining a capability of the sensor for measuring an environment of the vehicle 100.

The output over time 908A-C may correspond to an intensity or measurement unit (e.g., range, distance, speed, time of flight, etc.) of the detected sensor information over time. In some embodiments, the output over time 908A-C may include a number of outputs at times within the first detection point 904 and the last detection point 906. As a sensing environment changes over time (e.g., as targets move relative to the sensors) an intensity of the detected sensor information may change. For instance, when a vehicle 100 approaches an intersection and a target in front 110 of the vehicle 100, a RADAR sensor 116B may determine a range to the target by recording an intensity or measurement unit at various times the vehicle 100 is operating. In this example, as the vehicle 100 approaches the target, the range to the target decreases over time. In the event, that the output intensity or measurement unit is a time of flight associated with the emitted and sensed values, the graphical representations 901-903 would show a taller output at a first time (e.g., indicating that it took a long time for the a sensor emission to return back to the sensor) than a height of the output at a second or subsequent time (e.g., when the vehicle 100 and sensors are closer to the target). In the event, that the output intensity or measurement unit is an intensity of a returned sensor signal, the graphical representations 901-903 would show a shorter output at a first time (e.g., indicating that the sensor signal intensity measured from the return signal diminished some amount from the emitted signal intensity because the target was further away at the first time) than a height of the output at a second or subsequent time (e.g., when the vehicle 100 and sensors are closer to the target and the sensor signal intensity measured from the return signal was closer to the emitted signal intensity). In any event, the change in range to a target may be shown as a sensor output that changes in intensity associated with the output over time 908A-C.

FIG. 9A shows a graphical representation 901 of an output over time 908A for a first sensor of the vehicle 100. As shown in FIG. 9A, the output over time 908A may include varying levels of intensity or measurement units along the vertical axis 912 for one or more times in the horizontal axis 916. FIG. 9B shows a graphical representation 902 of an output over time 908B for a second sensor of the vehicle 100. As illustrated in FIGS. 9A-9B, the output over time 908A, 908B for the first and second sensors are substantially similar, if not identical. In some embodiments, the first and second sensors may be the same type of sensor (e.g., imaging and ranging system 112, sensors 116A-K, LIDAR 320, RADAR 324, ultrasonic 328, camera 332, infrared (IR) 336, and/or other sensor or system 338, etc.). For example, the first and second sensors may be RADAR sensors 324. Whenever the output over time 908A, 908B is substantially similar between sensors of the same type and/or location on a vehicle 100, the sensors may be determined to have the same operating characteristics or abilities. In one embodiment, this similarity may indicate that the sensors are unobstructed by any object.

FIG. 9C shows a graphical representation 903 of an output over time 908C for a third sensor of the vehicle 100. In some embodiments, one or more of the first and/or second sensors may be different from a third type of sensor for the vehicle 100. For instance, the third the same type of sensor may be an imaging sensor 116A, 116F, 332, 336 (e.g., a camera, etc.) of the vehicle 100. Although the output over time 908C is schematically represented as a 2D waveform, it should be appreciated that the visual data need not be so limited. In any event, the output over time 908C for the third sensor output is shown changing (e.g., in intensity and/or measurement unit, as described above) over time.

FIG. 10 shows a graphical representation 1001 illustrating an example of overlapped outputs over time 908B, 908C, 1008 for three sensors of the vehicle 100 over the same period of time. As described above, the methods and systems described herein may utilize sensor detection information that is similar, if not identical, to that shown in FIGS. 9A-10 (e.g., associated with one or more sensors to detect sensor obstructions including objects that are on, in contact with, or part of sensor surfaces. For example, the graphical representation 1001 of FIG. 10 shows an example of an output over time 1008 for a blocked first sensor. The first sensor in FIG. 10 may be determined to be blocked by comparing an output over time 908B for a similar sensor (e.g., second sensor) over a same time period. The output over time 908B for the second sensor is shown in dashed lines overlapping the output over time 1008 for the blocked first sensor. In this example graphical representation 1001, a difference between the outputs over time 1008, 908B may be determined or observed over a nonconforming region 1002 of the graph. As shown in FIG. 10, the first and second sensors provided detected sensor information that was similar, if not identical, over a first portion of the period of time (e.g., similar outputs over time 1008, 908B, over the portion of time). However, the first sensor provides different detected sensor information (e.g., output over time 1008) over a nonconforming region 1002 when compared to the second sensor output over time 908B for the same remaining portion of the period of time.

In some embodiments, the difference between the outputs over time 1008, 908B may indicate that at least one sensor of the vehicle 100 is obstructed and/or nonfunctional. It is an aspect of the present disclosure that a particular sensor, or sensors, may be identified as the obstructed sensor, or sensors. This identification may include referring to signal characteristics, intensities, measurement values, etc. associated with the sensors of the vehicle 100. In one embodiment, the sensor processors 340 may determine that the detected sensor information from one of the sensors is not changing according to a predicted, or preset, threshold. This lack of change in detected sensor information may indicate that the sensor is completely obstructed, or blocked, at or for an amount of time.

In some embodiments, the sensor processors 340 may determine that the detected sensor information from one of the sensors, when compared to the detected sensor information of at least one other sensor (e.g., a sensor of a different type, a third sensor, etc.) is not changing according to the change characteristics of the at least one other sensor. For instance, the third sensor providing the output over time 908C may be oriented in a similar position on the vehicle 100 (e.g., sensing movement, targets, or a change in environment around the vehicle 100, at a particular side, area, or zone of the vehicle 100, etc.) as the first and/or second sensors having output over time 1008, 908B. In this example, the sensor processors 340 may determine that the second sensor output over time 908B and the third sensor output over time 908C, while not necessarily identical, indicate a related change over time in the sensed environment. Additionally or alternatively, the sensor processors 340 may determine that the first sensor output over time 1008 and the third sensor output over time 908C have no relationship, at least over a portion of time (e.g., the nonconforming region 1002). In some embodiments, this relationship of change information may be used by the sensor processors 340 to uniquely identify the obstructed sensor from one or more sensors.

FIG. 11 shows a graphical representation 1101 illustrating an example of overlapped outputs over time 1108, 908B for multiple sensors of the vehicle 100 over the same period of time. As described above, the methods and systems described herein may utilize sensor detection information that is similar, if not identical, to that shown in FIGS. 9A-11 (e.g., associated with one or more sensors to detect sensor obstructions including objects that are on, in contact with, or part of sensor surfaces. In one example, a sensor may be obstructed by dirt or detritus and may provide information that is impaired in some way (e.g., not as accurate as a clean sensor, limited range of the sensor, etc.). For example, the graphical representation 1101 of FIG. 11 shows an example of an output over time 1108 for an obstructed first sensor. The first sensor in FIG. 11 may be determined to be obstructed by comparing an output over time 908B for a similar sensor (e.g., second sensor) over a same time period to the output over time 1108 for the first sensor. The output over time 908B for the second sensor is shown in dashed lines overlapping the output over time 1108 for the obstructed first sensor. In this example graphical representation 1101, a difference between the outputs over time 1108, 908B may be determined or observed over a nonconforming region 1102, or measurement variation, of the graph. As shown in FIG. 11, the first and second sensors provided detected sensor information that was similar, if not identical, over the period of time (e.g., similar outputs over time 1108, 908B). However, the first sensor provides a scaled (e.g., diminished, reduced, less accurate, etc.) measurement variation 1102 in the detected sensor information (e.g., output over time 1108) over the period of time when compared to the output over time 908B for the second sensor over the same period of time. In some embodiments, the measurement variation 1102 may be attributed to a proximity of a target to a particular sensor, but when the measurement variation 1102 (e.g., measurement offset, etc.) is substantially consistent across all measurements made over a period of time, the sensor may be determined to be obstructed (at least partially). In FIG. 11, for example, the sensor providing muted intensities or measurement values (e.g., reduced, lower, or diminished values, etc.) may be determined to be the sensor that is obstructed.

Figure 12A:
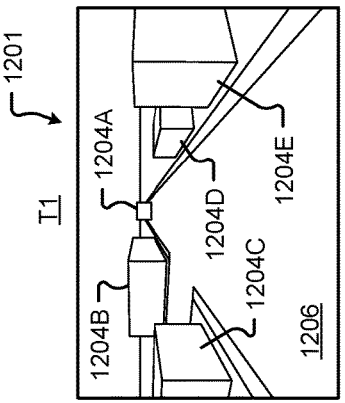
FIG. 12A shows a schematic view of imaging sensor information detected by an imaging system of the vehicle at a first time of travel in accordance with embodiments of the present disclosure.
Figure 12B:
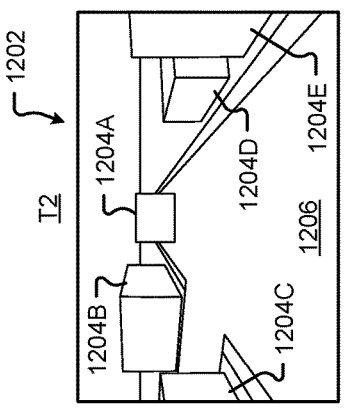
FIG. 12B shows a schematic view of imaging sensor information detected by an imaging system of the vehicle at a second time of travel in accordance with embodiments of the present disclosure.
Figure 12C:
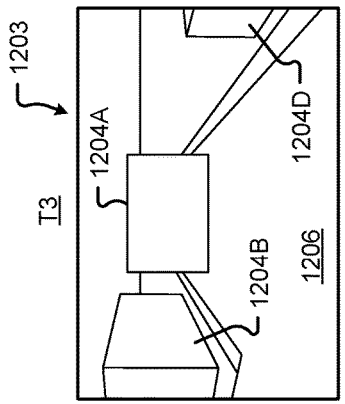
FIG. 12C shows a schematic view of imaging sensor information detected by an imaging system of the vehicle at a third time of travel in accordance with embodiments of the present disclosure.

Referring to FIGS. 12A-12C show schematic views of imaging sensor information 1201-1203, detected by at least one imaging system of the vehicle 100, describing a visual environment (e.g., at some point at or around the vehicle 100) that changes over time (T1-T3) (e.g., while the vehicle 100 is driving, etc.). In some embodiments, the imaging system may be one or more of the imaging sensors 116A, 116F, 332, 336 (e.g., a camera, etc.) described above. The schematic views of 12A-12C show computer-generated images 1201-1203 including one or more targets 1204A-E that are detected as changing in shape, size, range, and/or geometry while the vehicle 100 is operating along a path 1206 or roadway.

FIG. 12A shows a schematic view of imaging sensor information 1201 detected by the imaging system of the vehicle 100 at a first time of travel T1 in accordance with embodiments of the present disclosure. In some embodiments, the vehicle 100 may be driving down a street, roadway, or other driving path 1204. As the vehicle 100 is driving, the imaging system may visually detect targets in a sensing area of the imaging system describing (e.g., visually) an environment outside of the vehicle 100. The environment may include a first target 1204A (e.g., another vehicle, a pedestrian, an object, etc.) on the roadway 1206, and/or one or more other targets 1204B-E (e.g., buildings, landmarks, signs, markers, etc.).

As the vehicle 100 moves along the path 1206, visual characteristics associated with the targets 1204A-E may change at a second time T2. FIG. 12B shows a schematic view of imaging sensor information 1202 detected by the imaging system of the vehicle 100 at a second time of travel T2 in accordance with embodiments of the present disclosure. In FIG. 12B, the range to all of the targets 1204A-E has changed. For example, the size and shape of the vehicle target 1204 and the building targets 1204B, 1204D, 1204E have increased in dimension at the second time T2, while building target 1204C is shown moving off-image.

As the vehicle 100 continues to move along the path 1206 at a subsequent time, the visual characteristics associated with the targets 1204A-E may continue to change. In FIG. 12C, a schematic view of imaging sensor information 1203 detected by the imaging system of the vehicle 100 at a third time of travel T3 is shown in accordance with embodiments of the present disclosure. FIG. 12C shows that target information has changed to include a larger shape and size associated with some targets, while other targets have moved completely off-image. For instance, vehicle target 1204 and the building target 1204B have increased in shape and size, while building target 1204D is shown moving off-image and building targets 1204C, 1204E have moved completely off-image. In some embodiments, FIGS. 12A-12C show imaging sensor information changing over time (e.g., T1-T3) for an unobstructed imaging system and/or sensor.

Figure 13A:
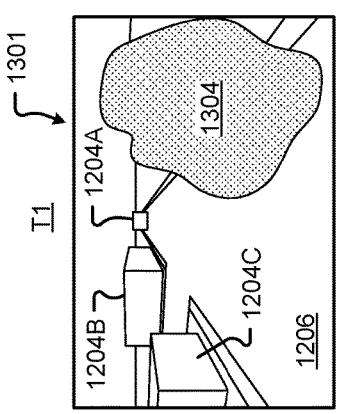
FIG. 13A shows a schematic view of obstructed imaging sensor information detected by an imaging system of the vehicle at a first time of travel in accordance with embodiments of the present disclosure.
Figure 13B:
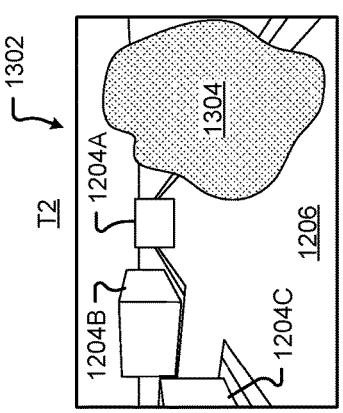
FIG. 13B shows a schematic view of obstructed imaging sensor information detected by an imaging system of the vehicle at a second time of travel in accordance with embodiments of the present disclosure.
Figure 13C:
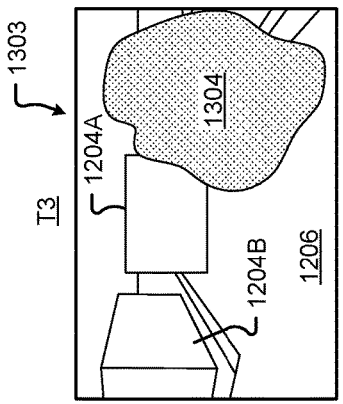
FIG. 13C shows a schematic view of obstructed imaging sensor information detected by an imaging system of the vehicle at a third time of travel in accordance with embodiments of the present disclosure.

FIGS. 13A-13C show schematic views of obstructed imaging sensor information 1301-1303, detected by at least one imaging system of the vehicle 100, describing a visual environment (e.g., at some point at or around the vehicle 100) that changes over time (T1-T3)(e.g., while the vehicle 100 is driving, etc.). In some embodiments, the imaging system may be one or more of the imaging sensors 116A, 116F, 332, 336 (e.g., a camera, etc.) described above. The schematic views of 13A-13C show computer-generated images 1301-1303 including one or more targets 1204A-C that are detected as changing in shape, size, range, and/or geometry and a region of the images that does not change while the vehicle 100 is operating along a path 1202 or roadway.

FIG. 13A shows a schematic view of obstructed imaging sensor information 1301 detected by the imaging system of the vehicle 100 at the first time of travel T1 in accordance with embodiments of the present disclosure. In one embodiment, the imaging system of the vehicle 100 shown in FIG. 13A may represent one camera or imaging sensor 116A, 116F, 332, 336 of the vehicle that has been exposed to an obstruction object 1304. The one camera or imaging sensor may be part of a combined imaging system (e.g., stereo cameras, 3D sensors, etc.) of the vehicle 100. In this example, the methods and systems described herein may compare imaging sensor information from one camera to the imaging sensor information from another camera in the combined imaging system to determine whether any camera in the combined imaging system is obstructed. For example, FIGS. 12A-12C may represent the unobstructed camera in the combined imaging system and FIGS. 13A-13C may represent the obstructed camera in the combined imaging system. In some embodiments, the obstruction object 1304 may be detected on a single imaging sensor and/or system.

In any event, the obstruction object 1304 may be any one or more of the objects described in conjunction with FIGS. 8A-8B. For instance, the imaging sensor information 1301 shown in FIG. 13A may represent an image of an environment associated with the vehicle 100 (e.g., around at least a portion of the vehicle 100, etc.) at the first time T1 when an obstruction object 1304 first appears in the computer-generated image 1301. At this point in time, the obstruction object 1304 may limit or obstruct a viewing or imaging capability of a region of the imaging system. For instance, targets 1204D, 1204E which were previously viewable are no longer viewable in the computer generated images 1301-1303 having the obstruction object 1304. This instantaneous replacement of a number of objects that were previously viewable in the computer-generated image 1301-1303 may indicate an obstruction object 1304 is obstructing the viewing capability of the imaging system.

In any event, as the vehicle 100 moves along the path 1206 at a second time T2, visual characteristics associated with the targets 1204A-C may change. However, targets that were previously viewable in a region of the image replaced by the obstruction object 1304 remain invisible to the imaging system shown in FIGS. 13A-13C. In one embodiment, the change in targets and non-change in the region of the image defined by the area of the obstruction object 1304 may indicate that an obstruction object 1304 is obstructing the viewing capability of the imaging system. This information may be used in conjunction with, or apart from, the instantaneous replacement of the number of objects described above in determining obstructions of sensors. In some cases, the images 1301-1303 of FIGS. 13A-13C may be compared to the images 1201-1203 of FIGS. 12A-12C to determine if an obstruction object 1304 is present. FIG. 13B shows a schematic view of imaging sensor information 1303 detected by the imaging system of the vehicle 100 at the second time of travel T2 in accordance with embodiments of the present disclosure. In FIG. 13B, the range to all of the visible targets 1204A-C has changed, but visual characteristics and information (e.g., size, shape, dimension, location, etc.) associated with the obstruction object 1304 has not substantially changed. For example, the size and shape of the vehicle target 1204 and the building target 1204B have increased in dimension at the second time T2 and the building target 1204C is shown moving off-image, but the obstruction object 1304 region has not changed.

As the vehicle 100 continues to move along the path 1206 at a subsequent time, the visual characteristics associated with the visible targets 1204A, 1204B may continue to change. In FIG. 13C, the schematic view of obstructed imaging sensor information 1303 detected by the imaging system of the vehicle 100 at a third time of travel T3 is shown in accordance with embodiments of the present disclosure. FIG. 13C shows that target information has changed to include a larger shape and size associated with some targets, while other targets have moved completely off-image, and the obstruction object 1304 has not substantially changed. For instance, vehicle target 1204 and the building target 1204B have increased in shape and size, while building target 1204C has moved completely off-image. In some embodiments, FIGS. 13A-13C show imaging sensor information changing over time (e.g., T1-T3) for an at least partially obstructed imaging system and/or sensor of the vehicle 100.

Figure 14:
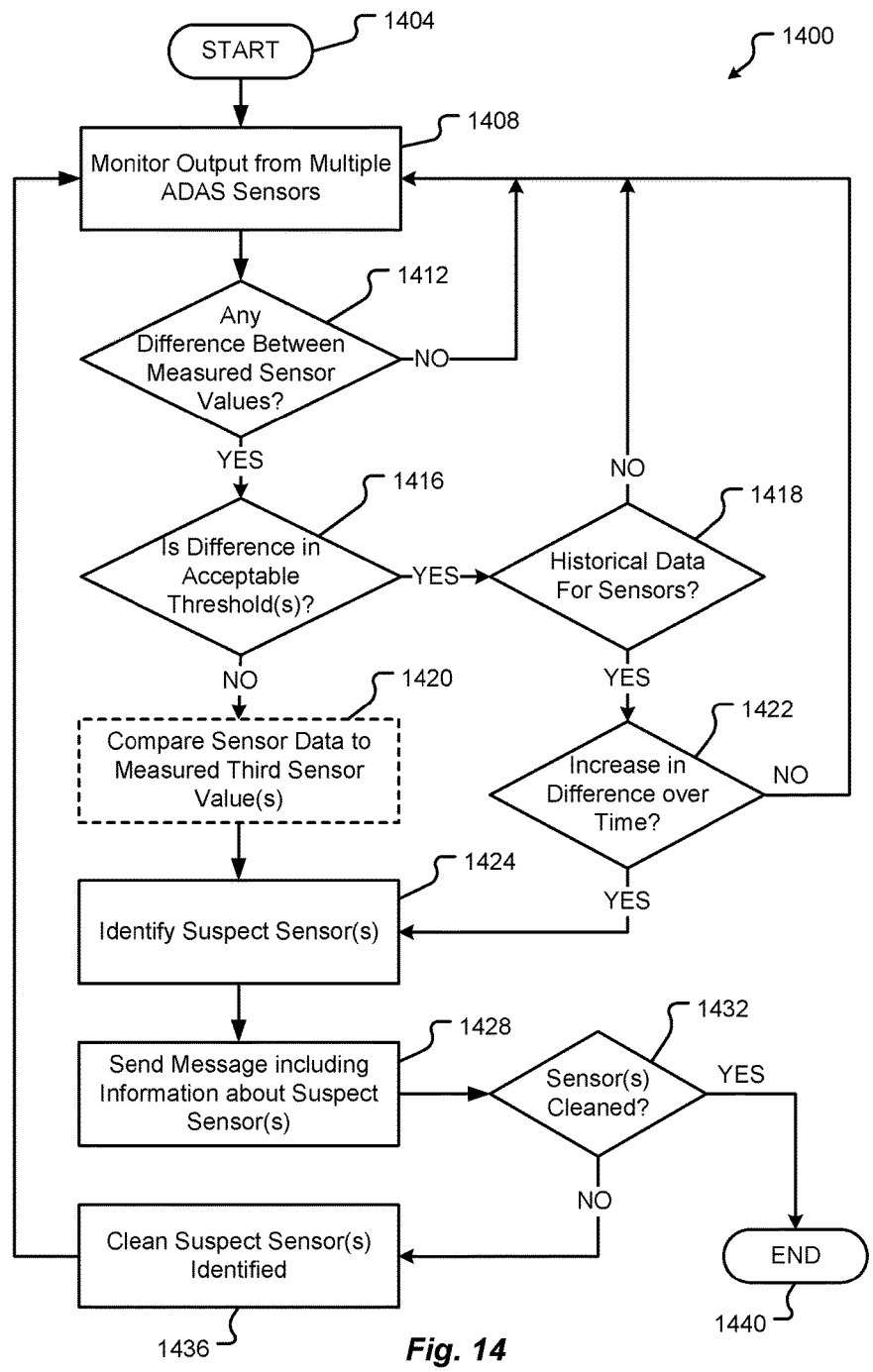
FIG. 14 is a flow diagram of a first method for detecting an object on a sensor surface of the vehicle in accordance with embodiments of the present disclosure.

FIG. 14 is a flow diagram of a first method 1400 for detecting an object on a sensor surface of the vehicle 100 in accordance with embodiments of the present disclosure. While a general order for the steps of the method 1400 is shown in FIG. 14, the method 1400 can include more or fewer steps or can arrange the order of the steps differently than those shown in FIG. 14. Generally, the method 1400 starts with a start operation 1404 and ends with an end operation 1440. The method 1400 can be executed as a set of computer-executable instructions executed by a computer system and encoded or stored on a computer readable medium. Hereinafter, the method 1400 shall be explained with reference to the systems, components, assemblies, devices, user interfaces, environments, software, etc. described in conjunction with FIGS. 1-13.

The method 1400 begins at step 1404 and proceeds by monitoring the sensor detection output from one or more sensors associated with the vehicle 100 (step 1408). In some embodiments, the sensors may be one or more of the ADAS vehicle sensors described above. In any event, the sensors may repeatedly, or continually, emit and receive sensing signals in an environment outside of the vehicle 100. In one embodiment, the monitoring may include a process of repeatedly receiving sensor information, interpreting the sensor information, and processing the sensor information. The sensor processor 340 described above may be configured to receive output from one or more sensors associated with the vehicle 100 and process the output. Typically, the sensors are disposed in, on, and/or about a vehicle 100 to, among other things, measure an environment around at least a portion of the vehicle 100 (e.g., a driving environment, parking environment, etc.). In some embodiments, sensor information and data may be stored in the sensor data memory 356A.

Next, the method 1400 continues by determining whether there are any differences between measured sensor values of one or more sensors (step 1412). Differences in measured sensor values may be obtained by comparing the output over time 908A-C, 1008, 1108 of sensors for a period of time, as described in conjunction with FIGS. 9A-11. For instance, a first sensor output over time 908A, 1008, 1108 for a period of time may be compared to another sensor output over time 908B, 908C for the same period of time. When the measure sensor values (e.g., the sensor outputs over time 908A-C, 1008, 1108) include substantial variation, a difference may be determined. In some embodiments, the differences in measured sensor values may include analyzing values of a single sensor over time. For example, the sensor output over time 908A-C, 1008, 1108 for a particular sensor, or sensor group, may include one or more data points that fail to meet a predetermined threshold. The predetermined threshold may be based on a timing associated with a return signal detected by the sensor, an intensity of the return signal detected, and/or combinations thereof. As one example, if the sensor emits a detection signal and instantaneously, or near-instantaneously, receives a response signal, the sensor may be determined to be obstructed. In this example, the time between emitting and receiving a sensor detection signal (e.g., time of flight) may be associated with a minimum threshold time. This minimum threshold time may be set to a time for the signal to return when a target is at the periphery of the vehicle 100, or at some offset of the periphery. In the event that a returned signal is received by the sensor faster than the minimum threshold time, then the sensor may be identified as obstructed and/or blocked. If there is no difference determined, the method 1400 returns to step 1408 to continue monitoring the sensor detection output by the sensors. In the event that a difference is determined to exist between measured sensor values, the method 1400 continues at step 1416.

The method 1400 proceeds by determining whether the differences determined in step 1412 are within acceptable thresholds of operation (step 1416). In some embodiments, a measurement variation 1102 may exist between the sensor output over time 908A-C, 1008, 1108 for a number of sensors. This measurement variation 1102 may be a drift, an offset measurement, and/or a nonconforming region 1002 variation. When a sensor is partially obstructed (e.g., via a minimal amount of debris, dust, or dirt etc.) the measurement variation 1102 may be within acceptable thresholds of operation. For example, an offset value of measurement may indicate that the obstructed sensor may not be as sensitive as a clean sensor but is still capable of making measurements according to a predetermined sensor measurement value or range. However, when a sensor includes a blocked portion, or a substantially obstructed sensor surface (e.g., the one or more surfaces of the sensor allowing the emission and detection of signals), the method may proceed to step 1420 and/or 1424.

In some embodiments, the method 1400 may optionally proceed to compare the sensor data (e.g., first and/or second sensor outputs over time 908A-B, 1008, 1108) of steps 1412 and 1416 to the sensor data (e.g., third sensor output over time 908C) of a third sensor. This comparison may be similar, if not identical, to the comparisons described in conjunction with FIGS. 9A-11.

Next, the method 1400 proceeds be identifying one or more sensors that are suspected of being dirty, unclean, and/or obstructed (step 1424). In some embodiments, the identification may be based on the comparison of step 1420 and/or the other steps of the method 1400 where a sensor is producing detected sensor information that fails to conform to the detected sensor information of other sensors (e.g., similar sensors, similarly positioned sensors, etc.). In one embodiment the differences in detected sensor information provided between sensors may be found to be outside acceptable thresholds of operation for a particular sensor. In some embodiments, where the difference between a first sensor and a second sensor is within acceptable thresholds of operation, the method 1400 may determine whether either or both of the first and second sensors are starting to fail, or drifting out of calibration (see steps 1418, 1422). For instance, in some embodiments, the differences determined between a sensor and another sensor may be compared to historical data associated with the sensors (step 1418). In some embodiments, once a sensor system is monitored and evaluated, the sensor data associated with that monitoring and evaluation may be stored in the sensor data memory 344. If the differences are determined to be increasing over time for a particular sensor, then that sensor may be determined to be failing or drifting out of calibration (1422). In any event, the method 1400 may identify a type, location, and/or position of the suspect sensor (i.e., the sensor(s) determined to be obstructed, failing, and/or drifting).

The method 1400 may proceed by sending a message including information about the suspect sensor to one or more of a user of the vehicle 100, a computing device 368, 604, 608, 612, a display device 372, a vehicle control system 348, and/or some other device associated with the vehicle 100 (step 1428). In some embodiments, the message may be configured to alert a user or other entity of a sensing obstruction associated with one or more sensors, indicate a severity of the obstruction, identify the sensor(s), and/or otherwise convey information about the sensor via a display device 372 associated with the vehicle 100. Additionally or alternatively, the message may include instructions and/or a command for the vehicle control system 348 and/or the sensor cleaning systems 370 of the vehicle 100 to clean the sensor identified. In some embodiments, the cleaning command may include information about a specific location and/or an area of the sensor surface that requires cleaning. For instance, in response to receiving the cleaning command, the sensor cleaning system 370 may determine a particular sensor cleaning device is associated with the identified sensor having the obstruction. Next, the sensor cleaning system 370 may send an electrical signal to the sensor cleaning device associated with the identified sensor having the obstruction to remove the obstruction.

Next, the method 1400 may continue by determining whether the vehicle control system 348 and/or the sensor cleaning systems 370 cleaned the sensor(s) (step 1432). In some embodiments, this determination may be made by proceeding through one or more the steps of the method 1400 to determine if the cleaning operation cured the detected measurement differences. In one embodiment, the sensor cleaning device or system may respond with an acknowledgement signal or message indicating that the cleaning operation was performed. If the sensor(s) have been previously cleaned a number of times and the cleaning still does not cure the detected measurement differences, the method 1400 may proceed by alerting the user or taking alternative action (not shown). In some embodiments, the method 1400 may determine that the identified sensors require additional cleaning (e.g., especially where a difference in measurement values improved from a first cleaning, etc.). In this instance, the method 1400 proceeds by cleaning the identified sensors via one or more sensor cleaning systems 370. The method ends at step 1440.

Figure 15:
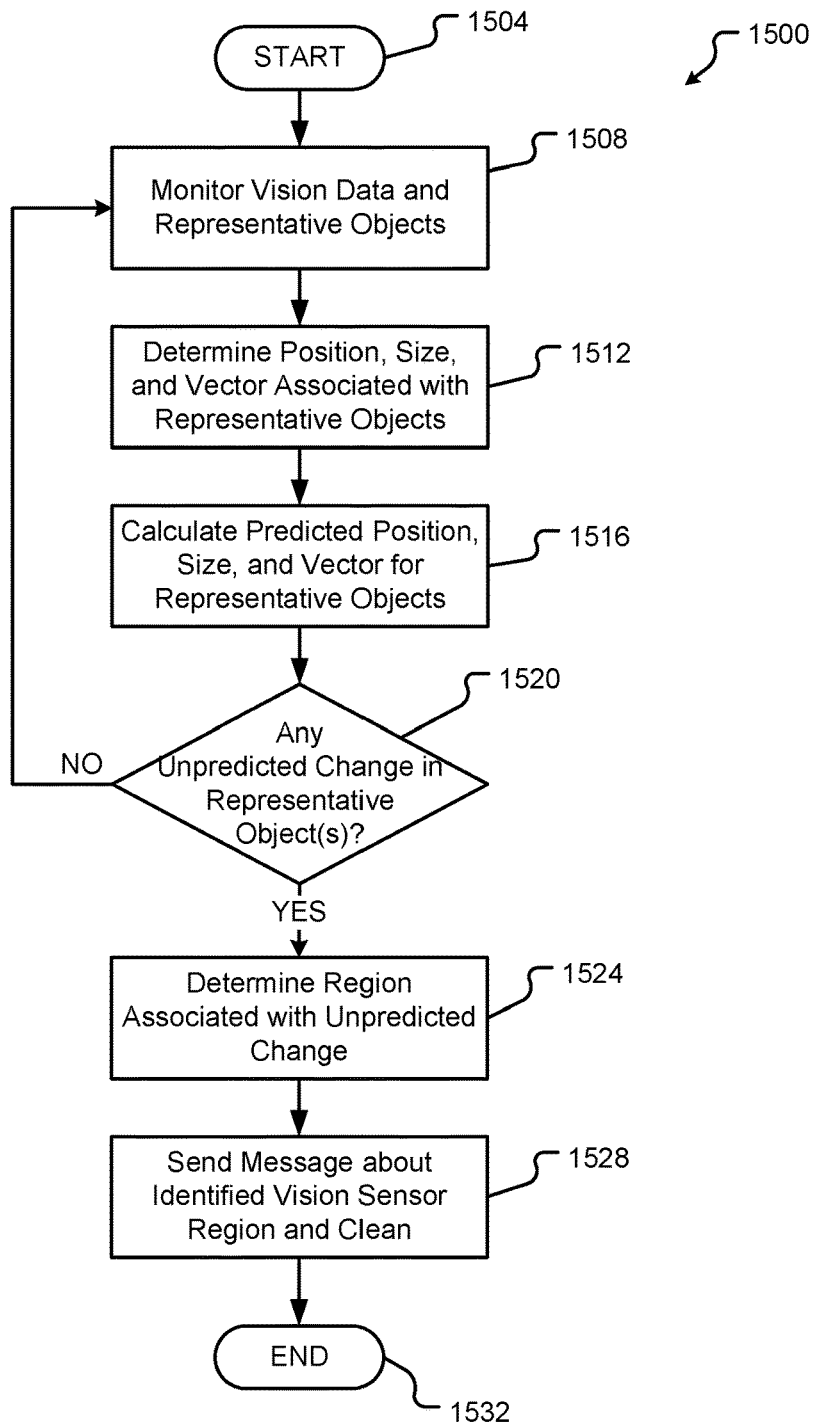
FIG. 15 is a flow diagram of a second method for detecting an object on a sensor surface of the vehicle in accordance with embodiments of the present disclosure.

FIG. 15 is a flow diagram of a second method 1500 for detecting an object on a sensor surface of the vehicle 100 in accordance with embodiments of the present disclosure. While a general order for the steps of the method 1500 is shown in FIG. 15, the method 1500 can include more or fewer steps or can arrange the order of the steps differently than those shown in FIG. 15. Generally, the method 1500 starts with a start operation 1504 and ends with an end operation 1540. The method 1500 can be executed as a set of computer-executable instructions executed by a computer system and encoded or stored on a computer readable medium. Hereinafter, the method 1500 shall be explained with reference to the systems, components, assemblies, devices, user interfaces, environments, software, etc. described in conjunction with FIGS. 1-14.

The method 1500 begins at step 1504 and proceeds by monitoring vision data and representative objects in computer-generated images from one or more imaging systems of the vehicle 100 (step 1508). In some embodiments, the imaging system may be one or more of the imaging sensors 116A, 116F, 332, 336 (e.g., a camera, etc.) described herein. The computer-generated image may correspond to one or more of the images 1201-1203, 1301-1303 described in conjunction with FIGS. 12A-13C. The monitoring may include receiving the information from one or more imaging system of the vehicle 100 and generating (e.g., via the sensor processors 340, etc.) one or more computer-generated images representing an environment around at least a portion of the vehicle 100.

Next, the method 1500 may continue by determining visual characteristics of targets in the computer-generated images (step 1512). For example, the method 1500 may determine a position, size, and/or a vector associated with one or more targets in the computer-generated images over time (e.g., T1-T3). For example, the method 1500 may determine that a vehicle 100 or other object is approaching the vehicle 100 along a particular path and speed.

In some embodiments, the method 1500 may calculate, based on the visual characteristics of the targets determined, at least one predicted position, size, and/or vector for the targets, or representative objects (step 1516). For instance, if the imaging sensor detects an target (e.g., vehicle target 1204A, etc.) getting closer and/or larger over time according to an observed speed and time, the sensor processors 340 may calculate, extrapolate, and/or otherwise determine a next position and/or size for the target at a subsequent or future time.

The method 1500 may continue by determining whether any subsequent changes to the targets or representative objects in the computer-generated images (e.g., generated from imaging sensor data and detected sensor information, etc.) are not substantially similar to the predicted position, size, and/or vector for the targets (step 1520). For instance, when an obstruction hits an imaging sensor, targets which were previously viewable in the computer-generated images may disappear, in an instant, or no longer be viewable. This instantaneous replacement of a number of targets or representative objects that were previously viewable in the computer-generated image may indicate an obstruction object 1304 is obstructing the viewing capability of the imaging system. For instance, a number of targets disappearing in an instant from the computer-generated image may not have been predicted in step 1516.

In the event, that there is an unpredicted change to one or more targets in the computer-generated images over time, the method 1500 may continue by determining the region of the imaging sensor associated with the unpredicted change (step 1524). In some embodiments, this determination may involve identifying one or more sensors in a group of sensors (e.g., combined image system, etc.) having the obstruction. In one embodiment, the determination may involve identifying a portion of the one or more sensors having the obstruction.

The method 1500 continues by sending a message about the identified imaging sensor (step 1528). In some embodiments, the message may direct a sensor cleaning system 370 to clean the identified imaging sensor having the obstruction. The message may include information about the identified imaging sensor to one or more of a user of the vehicle 100, a computing device 368, 604, 608, 612, a display device 372, a vehicle control system 348, and/or some other device associated with the vehicle 100 (step 1428). In response to receiving the cleaning command, the sensor cleaning system 370 may determine a particular sensor cleaning device is associated with the identified sensor having the obstruction. Next, the sensor cleaning system 370 may send an electrical signal to the sensor cleaning device associated with the identified sensor having the obstruction to remove the obstruction. In some embodiments, the message may be configured to alert a user or other entity of a sensing obstruction associated with one or more sensors, indicate a severity of the obstruction, identify the sensor(s), and/or otherwise convey information about the sensor via a display device 372 associated with the vehicle 100. Additionally or alternatively, the message may include instructions and/or a command for the vehicle control system 348 and/or the sensor cleaning systems 370 of the vehicle 100 to clean the sensor identified. In some embodiments, the cleaning command may include information about a specific location and/or an area of the sensor surface that requires cleaning. The method 1500 ends at step 1532.

The methods 1400, 1500 above describe sending messages about one or more obstructed, or suspect, sensors. In some embodiments, the one or more sensors may not be able to be cleaned and may remain obstructed. In some cases, an obstructed sensor may prevent a vehicle from operating safely in at least in one level of vehicle control. For instance, a vehicle 100 operating in a conditional, high, and/or full automation level (e.g., Levels 3-5) may require most of the sensors (e.g., especially the driving sensors and systems 304) to provide accurate and unobstructed information. Because some sensors may be more important than others, the sensor processors 340 and or vehicle control system may classify important sensors differently from other sensors. Important sensors may be treated differently by receiving prioritized attention (e.g., cleaning operations, maintenance, continual monitoring, etc.). Examples of important sensors in the automation context may include, but is not limited to, LIDAR 320, RADAR 324, ultrasonic 328, cameras 332, and/or IR sensors 336. In this case, the message may be sent to a vehicle control system 348 to limit a function of the vehicle 100, disable the vehicle 100, and/or present information to one or more devices of the vehicle 100 (e.g., requiring user intervention to replace and/or repair the identified sensor, etc.).

Figure 16A:
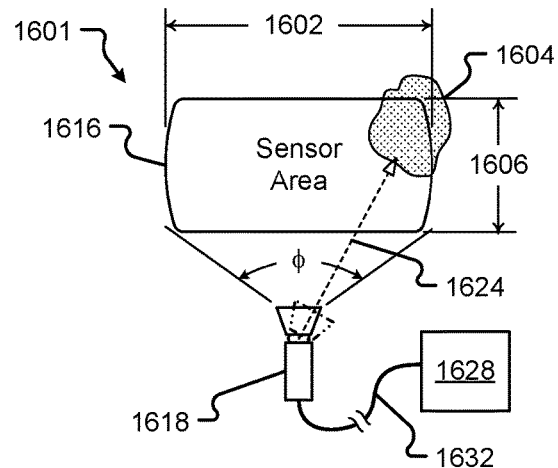
FIG. 16A shows a schematic view of a sensor cleaning system of the vehicle in accordance with embodiments of the present disclosure.
Figure 16B:
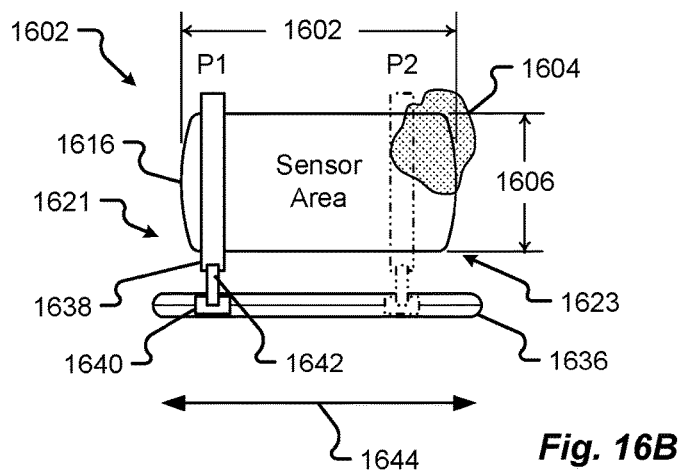
FIG. 16B shows a schematic view of a sensor cleaning system of the vehicle in accordance with embodiments of the present disclosure.
Figure 16C:
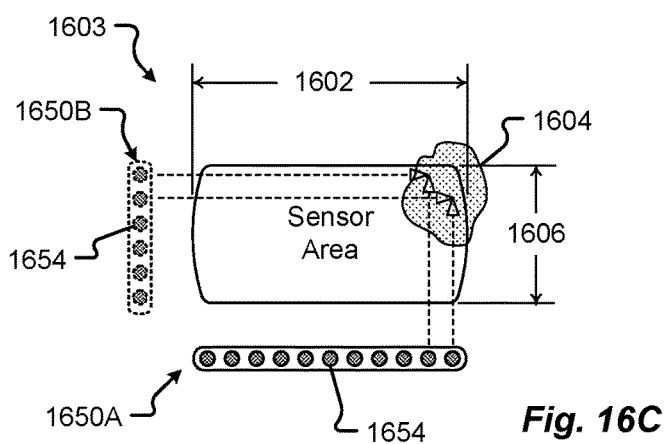
FIG. 16C shows a schematic view of a sensor cleaning system of the vehicle in accordance with embodiments of the present disclosure.

FIG. 16A-16C show schematic views of various sensor cleaning systems 1601-1603 of the vehicle 100 in accordance with embodiments of the present disclosure. The sensor cleaning systems 1601-1603 may correspond to the one or more of the sensor cleaning systems 370 described above. Each sensor cleaning system 1601-1603 shows an obstruction object 1604 at least partially obstructing a portion of the sensor surface 1616. As illustrated in FIGS. 16A-16C, a representative sensor surface 1616 is shown having a width 1602 and a height 1606 defining a sensor area of at least one sensor surface 1616 of the vehicle 100. The sensor surface 1616 may be associated with one or more of the sensors 112, 116A-K, 304, described above.

Referring now to FIG. 16A, a schematic view of a pressurized-fluid sensor cleaning system 1601 of the vehicle 100 is shown in accordance with embodiments of the present disclosure. The pressurized-fluid sensor cleaning system 1601 may include a fluid-directing nozzle 1618 configured to direct pressurized fluid supplied by fluid supply 1628 (e.g., a pump, or compressor, etc.) via one or more fluid lines 1632. The pressurized fluid may be directed (e.g., via the fluid-directing nozzle 1618) to clean the sensor area of the sensor surface 1616. In some embodiments, the fluid-directing nozzle 1618 may be moveable to target a particular region of the sensor area having the obstruction object 1604. For instance, a portion of the fluid-directing nozzle 1618 may be pivotable about an angular range defined by angle it, that encompasses the sensor area. The cleaning fluid may be compressed air or gas, pressurized water or other fluid, and/or some other focused fluid.

FIG. 16B shows a schematic view of an actuated-wiper sensor cleaning system 1602 of the vehicle 100 in accordance with embodiments of the present disclosure. The actuated-wiper sensor cleaning system 1602 may comprise a wiper blade 1638 attached to a moveable carriage 1640 via a connection arm 1642. The wiper blade 1638 may include a material that contacts the sensor area of the sensor surface 1616 to remove an obstruction object 1604. In some embodiments, the wiper blade 1638 may be made at least partially from a compliant material configured to conform to a shape, curve, or feature of the sensor surface 1616. Examples of the compliant material may include, but are in no way limited to, rubber, plastic, silicone, cloth, etc., and/or combinations thereof. The wiper blade 1638 may be configured to move from a first position P1 to a second position P2 in a wiper actuation. The wiper actuation may be in at least one direction along arrow 1644. In some embodiments, the moveable carriage 1640 of the actuated-wiper sensor cleaning system 1602 may be actuated via a solenoid, air/gas cylinder, hydraulic cylinder, screw actuator and motor, linear actuator, and/or any other actuator configured to convert energy into motion. For example, the moveable carriage 1640 may travel along a track 1636 associated with a body of the vehicle 100. In some embodiments, the wiper blade 1638 may be configured to move off of the sensor area to a first clear position 1621 (at the left-side of the sensor surface 1616) and/or to a second clear position 1623 (at the right-side of the sensor surface 1616). In the clear positions 1621, 1623 the complete sensor area is clear from obstruction by any component of the actuated-wiper sensor cleaning system 1602.

FIG. 16C shows a schematic view of a contactless sensor cleaning system 1603 of the vehicle 100 in accordance with embodiments of the present disclosure. In some embodiments, the contactless sensor cleaning system 1603 may comprise a first device 1650 comprising a horizontal array of ultrasonic transducers 1654 configured to emit ultrasonic pulses toward the sensor surface 1616 and remove an obstruction object 1604 therefrom. In one embodiment, a second device 1650B may comprise a vertical array of ultrasonic transducers 1654 (e.g., an array of ultrasonic transducers disposed orthogonal to the horizontal array, etc.) configured to emit ultrasonic pulses toward the sensor surface 1616 and remove an obstruction object 1604 therefrom. In some embodiments, both a first and second device 1650A, 1650B may be required to remove the obstruction object 1604 from the sensor surface 1616. For instance, when the ultrasonic pulses emitted by the first device 1650A intersect with ultrasonic pulses emitted by the second device 1650B, the pulse strength may reach a level of intensity required to move the object 1604. In any event, the contactless sensor cleaning system 1603 is configured to remove the obstruction object 1604 without physically touching the obstruction object 1604 and/or sensor surface 1616.

In one embodiment, one or more of the arrays of transducers 1654 may be replaced with one or more heating elements configured to heat the sensor area of the sensor surface 1616 to remove a particular type of obstruction object 1604 (e.g., ice, snow, hail, sleet, etc.) therefrom.

FIGS. 17A-17D show schematic plan and front views of a rotational-lens sensor cleaning system 1700A, 1700B (together 1700) of a vehicle 100 in accordance with embodiments of the present disclosure. The rotational-lens sensor cleaning system 1700 may correspond to the one or more of the sensor cleaning systems 370 described above. The rotational-lens sensor cleaning system 1700 shows an obstruction object 1604 at least partially obstructing a portion of the sensor surface 1616. As illustrated in FIG. 17A, a representative sensor surface 1616 is shown having a width 1602 and a height 1606 defining a sensor area of at least one sensor surface 1616 of the vehicle 100. The sensor surface 1616 may be associated with one or more of the sensors 112, 116A-K, 304, described above. The rotational-lens sensor cleaning system 1700 may include a rotating lens 1708 configured to rotate about a rotational axis 1706. In some embodiments, the sensor surface 1616 may correspond to a portion of the rotating lens 1708 that protrudes, or is exposed, from an opening in a sensor mount wall 1712A, 1712B

FIG. 17A shows a schematic plan and front view of components of a rotational-lens sensor cleaning system 1700A, 1700B of the vehicle 100 in accordance with embodiments of the present disclosure. In some embodiments, the rotational-lens sensor cleaning system 1700A, 1700B may include an internal sensor environment 1740 that is protected from an exterior environment 1738 (e.g., in an environment external to the vehicle 100, etc.) via at least one rotating lens 1708. The rotating lens 1708 may be configure to rotate about an axis 1706 in a clockwise and/or counterclockwise direction. In some embodiments, the rotating lens 1708 may be configured as a circular wall of sensor emission-transmissive (e.g., light transmissive, energy transmissive, transparent, etc.) material disposed around the internal sensor environment 1740 and where the sensor is directed toward a portion of the circular wall that is exposed to a sensing zone. In one embodiment, the movement of the rotating lens 1708 against a wiper portion of the left wall 1712A and/or a wiper portion of the right wall 1712B of a sensor viewing opening may cause the obstruction object 1604 to be removed from the sensor cleaning area of the sensor. In some embodiments, the rotating lens 1708 may move at least a portion of the lens 1708 into a lens cleaning area 1716 behind the sensor viewing opening in the walls 1712A, 1712B. The lens cleaning area 1716 may include a lens cleaning system 1720 comprising one or more of a pressurized-fluid unit 1724 (e.g., that is similar, if not identical, to the pressurized-fluid sensor cleaning system 1601 described in conjunction with FIG. 16A), a drive wheel 1728, and/or a wiper blade 1732. The lens cleaning system 1720 may wash a portion of the lens 1708 with the pressurized fluid as the lens 1708 is rotated behind the wall 1712A, 1712B. In some embodiments, the drive wheel 1728 may include a sponge, cloth, or other debris removal surface. The drive wheel 1728 may be attached to a motor or other actuator configured to rotate the drive wheel 1728 and the lens 1708. The wiper blade 1732 may be configured to contact the lens 1708 and remove any water and/or material that remains on the lens 1708 during a rotation thereby. In a 360-degree rotation, an obstructed lens 1708 may be washed, cleaned of the obstruction, and wiped dry for presentation in the sensor area.

FIG. 17B shows a schematic plan and front view of the rotational-lens sensor cleaning system 1700 in a first cleaning state 1701. In some embodiments, the first cleaning state 1701 may correspond to a point in time when an obstruction object 1604 is detected (e.g., in accordance with the methods 1400, 1500 described above) in a sensor area of a sensor.

FIG. 17C shows a second cleaning state 1702 for the rotational-lens sensor cleaning system 1700 upon receiving a cleaning message or command. For instance, the lens 1708 is rotating clockwise about the rotational axis 1706 and a first portion 1604A of the obstruction object 1604 is separated from a second portion 1604B of the obstruction object 1604. The first portion 1604A may be the only portion of the obstruction object 1604 that is on the lens 1708. The second portion 1604B may remain on a wall (e.g., the right wall 1712B) of the sensor mount outside the lens 1708 and sensor area. As shown in the schematic plan view of FIG. 17C, the lens 1708 is moving (from right to left) along the arrow shown.

FIG. 17D shows a third cleaning state 1703 for the rotational-lens sensor cleaning system 1700 continuing to index the lens rotationally about the rotational axis 1706. As the lens 1708 continues to rotate clockwise about the rotational axis 1706 the first portion 1604A of the obstruction object 1604 continues to move further from the second portion 1604B of the obstruction object 1604. In the schematic plan view of FIG. 17D, the lens 1708 is continuing to move (from right to left) along the arrow shown. Once the lens 1708 rotates past the wall 1712A, the sensor area may be clean from obstruction.

FIGS. 18A-18C show schematic cross-sectional views of a sensor cleaning system 1800 in various cleaning states 1801-1803. The sensor cleaning system 1800 may include at least one sensor and sensor surface 1816 mounted to an actuator 1820. The actuator 1820 may be configured to move the sensor and sensor surface 1816 from an exposed, or sensing, position to a concealed, or cleaning/protection, position via moving member 1824. In some embodiments, the actuator 1820 may be a solenoid, air/gas cylinder, linear actuator, screw actuator, hydraulic cylinder, and/or other actuator configured to convert energy into motion. The sensor cleaning system 1800 may include a sensor mount or vehicle body wall 1812A, 1812B having a sensor viewing window 1804 disposed therethrough. In some embodiments, the sensor and sensor surface 1816 may be exposed to the window 1804 to allow sensing and may be concealed behind a portion of the sensor cleaning system 1800 and/or window 1804 to clean and/or protect the sensor and sensor surface 1816.

The sensor cleaning system 1800 may include at least one cleaning wiper 1814A, 1814B pivotally arranged to clean the sensor and sensor surface 1816 when retracted (e.g., moved behind the wall 1812A, 1812B. In some cases, the at least one cleaning wiper 1814A, 1814B may be operatively connected to a spring element 1818A, 1818B. The spring element 1818A, 1818B may provide the force required to move the at least one cleaning wiper 1814A, 1814B against a portion of the sensor and sensor surface 1816. This movement may clean an obstruction object from the sensor and sensor surface 1816 via a wiping action.

FIG. 18A shows a schematic cross-sectional view of the sensor cleaning system 1800 and a sensor 1816 of the vehicle 100 in a first cleaning state 1801 in accordance with embodiments of the present disclosure. In the first cleaning state 1801, the actuator 1820 may position the sensor and sensor surface 1816 in an exposed, or sensing, position. In this position, the sensor and sensor surface 1816 may have an unobstructed viewing angle. In one embodiment, a portion of the at least one cleaning wiper 1814A, 1814B may be connected via a spring element 1818A, 1818B in tension and connected to the wall 1812A, 1812B. The tension of the spring element 1818A, 1818B may provide a contact force of the at least one cleaning wiper 1814A, 1814B against the sensor and sensor surface 1816.

FIG. 18B shows a schematic cross-sectional view of the sensor cleaning system 1800 and a sensor 1816 of the vehicle 100 in a second cleaning state 1802 in accordance with embodiments of the present disclosure. In the second cleaning state 1802, the sensor cleaning system 1800 may have received an instruction (e.g., as described above) to retract (e.g., in a direction indicated by the arrow of the moving member 1824) from the exposed, or sensing, position. As the sensor and sensor surface 1816 retracts, via an actuation motion imparted by the actuator 1820, the tension of the spring elements 1818A, 1818B acting on the first and second cleaning wipers 1814A, 1814B moves the first and second cleaning wipers 1814A, 1814B about a pivot point (not shown). The movement of the first and second cleaning wipers 1814A, 1814B causes the sensor and sensor surface 1816 to be cleaned via a wiping or dragging action. In the second cleaning state 1802, a portion of the sensor and sensor surface 1816 may be visible in the window 1804.

FIG. 18C shows a schematic cross-sectional view of the sensor cleaning system 1800 and a sensor 1816 of the vehicle 100 in a third cleaning state 1803 in accordance with embodiments of the present disclosure. In the third cleaning state 1803, the sensor cleaning system 1800 has retracted to its cleaned and/or concealed/protected position. In this position, any obstructive object on a portion of the sensor and sensor surface 1816 has been wiped clean and the sensor and sensor surface 1816 is protected behind the first and second cleaning wipers 1814A, 1814B. It is anticipated, that the sensor cleaning system 1800 described herein may protect a sensor 1816 from damage by retracting behind the first and second cleaning wipers 1814A, 1814B. In one embodiment, this retraction may be caused by detecting an impending impact, etc. This action may correspond to a sensor blinking.

Figure 19A:
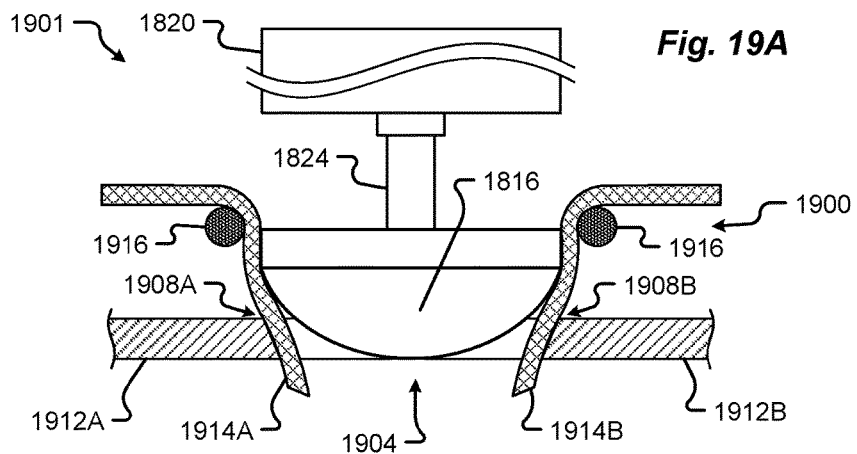
FIG. 19A shows a schematic cross-sectional view of a sensor cleaning system and sensor of the vehicle in a first cleaning state in accordance with embodiments of the present disclosure.
Figure 19B:
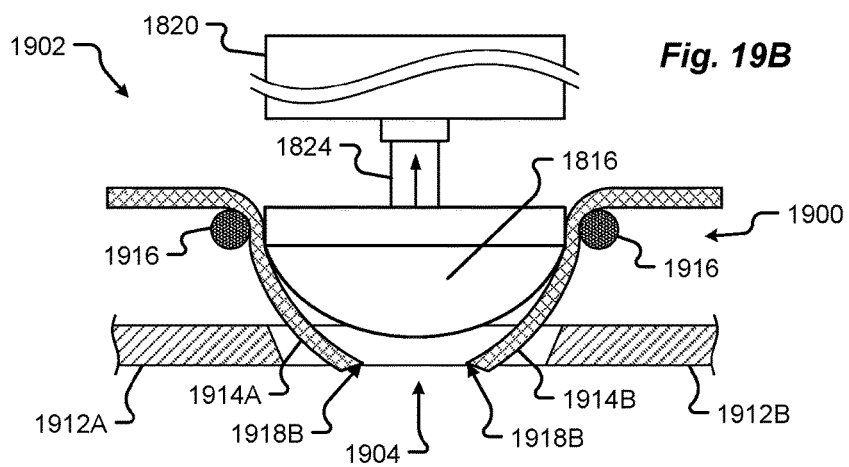
FIG. 19B shows a schematic cross-sectional view of a sensor cleaning system and sensor of the vehicle in a second cleaning state in accordance with embodiments of the present disclosure.
Figure 19C:
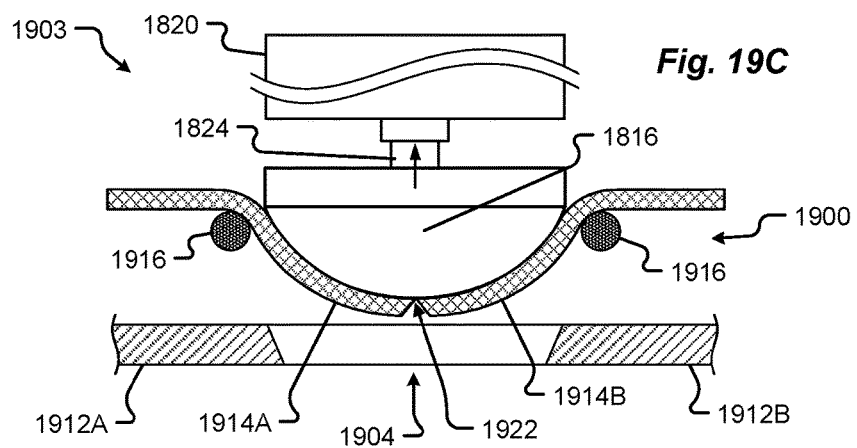
FIG. 19C shows a schematic cross-sectional view of a sensor cleaning system and sensor of the vehicle in a third cleaning state in accordance with embodiments of the present disclosure.

FIGS. 19A-19C show schematic cross-sectional views of a sensor cleaning system 1900 in various cleaning states 1901-1903. The sensor cleaning system 1900 may include at least one sensor and sensor surface 1816 mounted to an actuator 1820. The actuator 1820 may be configured to move the sensor and sensor surface 1816 from an exposed, or sensing, position to a concealed, or cleaning/protection, position via moving member 1824. In some embodiments, the actuator 1820 may be a solenoid, air/gas cylinder, linear actuator, screw actuator, hydraulic cylinder, and/or other actuator configured to convert energy into motion. The sensor cleaning system 1900 may include a sensor mount or vehicle body wall 1912A, 1912B having a sensor viewing window 1904 disposed therethrough. In some embodiments, the sensor and sensor surface 1816 may be exposed to the window 1904 to allow sensing and may be concealed behind a portion of the sensor cleaning system 1900 and/or the window 1904 to clean and/or protect the sensor and sensor surface 1816.

The sensor cleaning system 1900 may include at least one flexible cleaning wiper 1914A, 1914B that is configured to elastically bend about a member 1916. The flexible cleaning wipers 1914A, 1914B may be made of one or more compliant materials. Examples of compliant materials may include, but are in no way limited to, rubber, plastic, silicone, polymers, neoprene, spring steel, etc., and/or combinations thereof. The flexible cleaning wipers 1914A, 1914B may be portions of a single piece of flexible material that is split at an area of the sensor 1816. For example, the split may correspond to one or more cuts in the flexible material separating the single piece of material into two or more flexible cleaning wipers 1914A, 1914B. In some embodiments, the member 1916 may be a ring, hole, cutout, or other structure behind the sensor mount or vehicle body wall 1912A, 1912B. As the flexible cleaning wiper 1914A, 1914B is deflected (e.g., elastically deforms) between the member 1916 and the sensor and sensor surface 1816, a first flexible cleaning wiper 1914A may separate from a second cleaning wiper 1914B. As the sensor and sensor surface 1816 is retracted from the window 1904, the first and second flexible cleaning wipers 1914A, 1914B may return to an undeflected, or less-deflected, state. In the less-deflected state, a portion of the flexible cleaning wipers 1914A, 1914B (e.g., wiper tips 1918A, 1918B) may contact a portion of the sensor and sensor surface 1816. This movement may clean an obstruction object from the sensor and sensor surface 1816 via a wiping action.

FIG. 19A shows a schematic cross-sectional view of the sensor cleaning system 1900 and a sensor 1816 of the vehicle 100 in a first cleaning state 1901 in accordance with embodiments of the present disclosure. In the first cleaning state 1901, the actuator 1820 may position the sensor and sensor surface 1816 in an exposed, or sensing, position. In this position, the sensor and sensor surface 1816 may have an unobstructed viewing angle. In one embodiment, a portion of the flexible cleaning wipers 1914A, 1914B may be elastically deformed, or deflected, against a portion of the window 1904.

FIG. 19B shows a schematic cross-sectional view of the sensor cleaning system 1900 and a sensor 1816 of the vehicle 100 in a second cleaning state 1902 in accordance with embodiments of the present disclosure. In the second cleaning state 1902, the sensor cleaning system 1900 may have received an instruction (e.g., as described above) to retract (e.g., in a direction indicated by the arrow of the moving member 1824) from the exposed, or sensing, position. As the sensor and sensor surface 1816 retracts, via an actuation motion imparted by the actuator 1820, the elasticity of the flexible cleaning wipers 1914A, 1914B causes the wipers 1914A, 1914B to follow the movement of the sensor and sensor surface 1816. This movement of the wipers 1914A, 1914B causes the sensor and sensor surface 1816 to be cleaned via a wiping or dragging action of a portion (e.g., the wiping portion 1918A, 1918B, etc.) of the wipers 1914A, 1914B contacting the surface 1816. In the second cleaning state 1902, a portion of the sensor and sensor surface 1816 may still be visible in the window 1904.

FIG. 19C shows a schematic cross-sectional view of the sensor cleaning system 1900 and a sensor 1816 of the vehicle 100 in a third cleaning state 1903 in accordance with embodiments of the present disclosure. In the third cleaning state 1903, the sensor cleaning system 1900 has retracted to its cleaned and/or concealed/protected position. In this position, any obstructive object on a portion of the sensor and sensor surface 1816 has been wiped clean and the sensor and sensor surface 1816 is protected behind the first and second flexible cleaning wipers 1914A, 1914B. It is anticipated, that the sensor cleaning system 1900 described herein may protect a sensor 1816 from damage by retracting behind the first and second flexible cleaning wipers 1914A, 1914B. In one embodiment, this retraction may be caused by detecting an impending impact, etc.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include a method, comprising: receiving, via a processor, output from sensors of a vehicle monitoring an environment around a portion of the vehicle; determining, via the processor, a first output over time for a first sensor of the sensors of the vehicle; determining, via the processor, a second output over time for a second sensor of sensors of the vehicle; identifying, via the processor and based on sensor information in the first output over time and the second output over time, an obstructed sensor from at least one of the first sensor and/or the second sensor; and sending, via the processor, a message including information about the obstructed sensor to one or more devices of the vehicle.

Aspects of the above method include wherein the message instructs a sensor cleaning system of the vehicle to clean the obstructed sensor identified. Aspects of the above method include wherein the sensor information in the first output over time includes a time of flight defining a time for a detection signal emitted by the first sensor to be detected by the first sensor. Aspects of the above method include wherein a time of flight minimum threshold is defined as an amount of time for the first sensor to detect a target at a periphery of a body of the vehicle, and wherein the first sensor is identified as the obstructed sensor based on the time of flight in the first output over time being less than the time of flight minimum threshold. Aspects of the above method include wherein identifying the obstructed sensor further comprises: determining, via the processor, that the first sensor and the second sensor are a same type of sensor; comparing, via the processor, the first output over time to the second output over time; and determining, via the processor, at least one difference between the first output over time and the second output over time. Aspects of the above method further comprise: determining, via the processor, a third output over time for a third sensor of the sensors of the vehicle, wherein the third sensor is a different type of sensor from the first and second sensors; comparing, via the processor, detection characteristics of the third output over time to detection characteristics for each of the first output over time and the second output over time; and determining, via the processor, the obstructed sensor is at least one of the first sensor and/or the second sensor when the detection characteristics of the third output over time fail to match the detection characteristics for the first output over time and/or the second output over time. Aspects of the above method include wherein the first sensor is an imaging sensor and the first output over time includes first computer-generated images of the environment around the portion of the vehicle over time, and wherein the second sensor is an imaging sensor and the second output over time includes second computer-generated images of the environment around the portion of the vehicle over time. Aspects of the above method include wherein identifying the obstructed sensor further comprises: determining, via the processor, a position and size for targets in the first and second computer-generated images over time, wherein the targets represent objects in the environment around the portion of the vehicle. Aspects of the above method include wherein identifying the obstructed sensor further comprises: determining, via the processor, the obstructed sensor is one of the first sensor or the second sensor when at least one of the targets in one of the first and second computer-generated images over time is not present in the other of the first and second computer-generated images over time. Aspects of the above method include wherein identifying the obstructed sensor further comprises: determining, via the processor and based on the position and size for the targets, a predicted position and size for the targets at a subsequent time. Aspects of the above method include wherein identifying the obstructed sensor further comprises: determining, via the processor, a subsequent position and size for the targets in subsequent first and second computer-generated images over time; and determining, via the processor, the obstructed sensor is at least one of the first sensor and/or the second sensor when the subsequent position and size for the targets in subsequent first and/or second computer-generated images over time fail to match the predicted position and size for the targets at the subsequent time.

Embodiments include a vehicle, comprising: at least one sensor; a microprocessor coupled to the at least one sensor; and a computer readable medium coupled to the microprocessor and comprising instructions stored thereon that cause the microprocessor to: receive output from the at least one sensor monitoring an environment around a portion of the vehicle; determine a first output over time for a first sensor of the at least one sensor; determine a second output over time for a second sensor of the at least one sensor; identify, based on sensor information in the first output over time and the second output over time, an obstructed sensor from at least one of the first sensor and/or the second sensor; and send a message including information about the obstructed sensor to one or more devices of the vehicle.

Aspects of the above vehicle further comprise: a sensor cleaning system including one or more components that clean the at least one sensor of the vehicle, and wherein the message is sent to the sensor cleaning system to clean the obstructed sensor identified. Aspects of the above vehicle include wherein the sensor information in the first output over time includes a time of flight defining a time for a detection signal emitted by the first sensor to be detected by the first sensor. Aspects of the above vehicle include wherein a time of flight minimum threshold is defined as an amount of time for the first sensor to detect a target at a periphery of a body of the vehicle, and wherein the first sensor is identified as the obstructed sensor based on the time of flight in the first output over time being less than the time of flight minimum threshold. Aspects of the above vehicle include wherein the first sensor is an imaging sensor and the first output over time includes first computer-generated images of the environment around the portion of the vehicle over time, and wherein the second sensor is an imaging sensor and the second output over time includes second computer-generated images of the environment around the portion of the vehicle over time. Aspects of the above vehicle include wherein in identifying the obstructed sensor the instructions further cause the microprocessor to: determine a position and size for targets in the first and second computer-generated images over time, wherein the targets represent objects in the environment around the portion of the vehicle; and determine the obstructed sensor is one of the first sensor or the second sensor when at least one of the targets in one of the first and second computer-generated images over time is not present in the other of the first and second computer-generated images over time.

Embodiments include a device, comprising: a microprocessor; and a computer readable medium coupled to the microprocessor and comprising instructions stored thereon that cause the microprocessor to: receive output from sensors of a vehicle monitoring an environment around a portion of the vehicle; determine a first output over time for a first sensor of the sensors of the vehicle; determine a second output over time for a second sensor of sensors of the vehicle; identify, based on sensor information in the first output over time and the second output over time, an obstructed sensor from at least one of the first sensor and/or the second sensor; and send a message including information about the obstructed sensor to one or more devices of the vehicle.

Aspects of the above device include wherein the message instructs a sensor cleaning system of the vehicle to clean the obstructed sensor identified. Aspects of the above device include wherein the instructions cause the microprocessor to render at least a portion of the information about the obstructed sensor to a display device of the vehicle.

Embodiments include a sensor cleaning system, comprising: at least one sensor cleaning device including an obstruction cleaning element; a microprocessor; and a computer readable medium coupled to the microprocessor and comprising instructions stored thereon that cause the microprocessor to: communicate with a sensor processor of a vehicle, wherein the sensor processor receives output from sensors of the vehicle monitoring an environment outside of the vehicle; receive a cleaning command from the sensor processor identifying a sensor of the vehicle having an obstructed sensor surface; determine a sensor cleaning device associated with the identified sensor from the at least one sensor cleaning device; and send an electrical signal to the determined sensor cleaning device associated with the identified sensor, wherein the electrical signal actuates the obstruction cleaning element of the determined sensor cleaning device.

Aspects of the above sensor cleaning system include wherein the determined sensor cleaning device is a pressurized-fluid sensor cleaning device, comprising: a fluid-directing nozzle configured to direct a pressurized fluid toward the obstructed sensor surface of the identified sensor; a fluid supply configured to contain the pressurized fluid; and a fluid line operatively attached between the fluid-directing nozzle and the fluid supply, wherein the fluid line is configured to convey pressurized fluid from the fluid supply to the fluid-directing nozzle. Aspects of the above sensor cleaning system include wherein the pressurized fluid is a gas, and wherein the fluid supply comprises a compressor. Aspects of the above sensor cleaning system include wherein the determined sensor cleaning device is an actuated-wiper sensor cleaning device, comprising: a track disposed adjacent to the identified sensor; a carriage configured to move along a length of the track; a wiper blade operatively connected to the carriage and configured to move with the carriage; and an actuator configured to convert the electrical signal sent by the microprocessor into a mechanical motion of the carriage along the length of the track and causing the wiper blade to contact a portion of the sensor surface and clear the obstruction. Aspects of the above sensor cleaning system include wherein the determined sensor cleaning device is a contactless sensor cleaning device, comprising: a first array of ultrasonic transducers disposed adjacent to the identified sensor, wherein each ultrasonic transducer in the first array of ultrasonic transducers is configured to selectively emit first ultrasonic pulses toward the obstructed sensor surface of the identified sensor. Aspects of the above sensor cleaning system further comprise: a second array of ultrasonic transducers disposed adjacent to the identified sensor and orthogonal to the first array of ultrasonic transducers, wherein each ultrasonic transducer in the second array of ultrasonic transducers is configured to selectively emit second ultrasonic pulses toward the obstructed sensor surface of the identified sensor, and wherein a force of the first ultrasonic pulses and the second ultrasonic pulses is multiplied at an intersection of first and second ultrasonic pulses emitted. Aspects of the above sensor cleaning system include wherein the determined sensor cleaning device is a rotational-lens sensor cleaning device, comprising: a lens having a substantially circular outer periphery and a hollow internal portion defining an interior sensor environment configured to receive at least one sensor of the vehicle, and wherein the obstructed sensor surface is on a portion of the circular outer periphery of the lens; a motorized rotation drive wheel operatively connected to the lens and configured to rotate the lens about an axis of rotation; and at least one wiping element in contact with the circular outer periphery of the lens, wherein the lens is configured to rotate relative to the at least one wiping element. Aspects of the above sensor cleaning system include wherein a portion of the rotational-lens sensor cleaning device is disposed inside a body of the vehicle, and wherein the at least one wiping element is attached to the body of the vehicle. Aspects of the above sensor cleaning system include further comprise: a lens cleaning system, comprising: a pressurized-fluid nozzle configured to direct a pressurized fluid toward the lens; and a debris removal surface disposed adjacent to the pressurized-fluid nozzle and in contact with the lens. Aspects of the above sensor cleaning system include wherein the determined sensor cleaning device comprises: at least one wiping element in contact with the sensor surface of the identified sensor; and an actuator attached to a portion of the identified sensor and configured to move the portion of the identified sensor relative to the at least one wiping element, the actuator having an extended sensor position and a retracted sensor position, and wherein the at least one wiping element is configured to move across a portion of the sensor surface of the identified sensors as the actuator moves between the extended sensor position and the retracted sensor position. Aspects of the above sensor cleaning system include wherein the at least one wiping element pivots about an axis as the actuator moves between the extended sensor position and the retracted sensor position. Aspects of the above sensor cleaning system include wherein the at least one wiping element is maintained in contact with the sensor surface of the identified sensor via a force from a spring element connected between the at least one wiping element and a fixed wall. Aspects of the above sensor cleaning system include wherein in the retracted sensor position the identified sensor is protected from an exterior environment associated with the vehicle by the at least one wiping elements. Aspects of the above sensor cleaning system include wherein the at least one wiping element is a flexible material that is configured to elastically deform and create an opening therein exposing a viewing portion of the identified sensor when the actuator is in the extended sensor position and conceal the viewing portion of the identified sensor when the actuator is in the retracted sensor position.

Embodiments include a vehicle, comprising: at least one sensor monitoring an environment outside of the vehicle; and a sensor cleaning system, comprising: at least one sensor cleaning device of the vehicle including an obstruction cleaning element; a microprocessor; and a computer readable medium coupled to the microprocessor and comprising instructions stored thereon that cause the microprocessor to: communicate with a sensor processor of the vehicle, wherein the sensor processor receives output from the at least one sensor of the vehicle; receive a cleaning command from the sensor processor identifying a sensor of the at least one sensor of the vehicle having an obstructed sensor surface; determining a sensor cleaning device associated with the identified sensor from the at least one sensor cleaning device; and sending an electrical signal to the determined sensor cleaning device associated with the identified sensor, wherein the electrical signal actuates the obstruction cleaning element of the determined sensor cleaning device.

Aspects of the above vehicle include wherein the determined sensor cleaning device is a contactless sensor cleaning device, comprising: a first array of ultrasonic transducers disposed adjacent to the identified sensor, wherein each ultrasonic transducer in the first array of ultrasonic transducers is configured to selectively emit first ultrasonic pulses toward the obstructed sensor surface of the identified sensor. Aspects of the above vehicle include wherein the determined sensor cleaning device is a rotational-lens sensor cleaning device, comprising: a lens having a substantially circular outer periphery and a hollow internal portion defining an interior sensor environment configured to receive the one or more sensors of the vehicle, and wherein the obstructed sensor surface is on a portion of the circular outer periphery of the lens; a motorized rotation drive wheel operatively connected to the lens and configured to rotate the lens about an axis of rotation; and at least one wiping element in contact with the circular outer periphery of the lens, wherein the lens is configured to rotate relative to the at least one wiping element. Aspects of the above vehicle include wherein the determined sensor cleaning device comprises: at least one wiping element in contact with the sensor surface of the identified sensor; and an actuator attached to a portion of the identified sensor and configured to move the portion of the identified sensor relative to the at least one wiping element, the actuator having an extended sensor position and a retracted sensor position, and wherein the at least one wiping element is configured to move across a portion of the sensor surface of the identified sensors as the actuator moves between the extended sensor position and the retracted sensor position. Aspects of the above vehicle include wherein a viewing portion of the identified sensor is exposed to an environment external to the vehicle when the actuator is in the extended sensor position and wherein the viewing portion of the identified sensor is concealed from the environment external to the vehicle when the actuator is in the retracted sensor position.

Embodiments include a sensor cleaning device of a vehicle, comprising: at least one vehicle sensor cleaning element; a microprocessor; and a computer readable medium coupled to the microprocessor and comprising instructions stored thereon that cause the microprocessor to: receive an electrical signal from a sensor cleaning system of a vehicle, wherein the electrical signal actuates the at least one vehicle sensor cleaning element; determine whether the at least one vehicle sensor cleaning element actuated; and send a message to the sensor cleaning system of the vehicle including information about the determination.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. A method, comprising:
receiving, via a processor, output from sensors of a vehicle monitoring an environment around a portion of the vehicle;
determining, via the processor, a first output over time for a first sensor of the sensors of the vehicle;
determining, via the processor, a second output over time for a second sensor of the sensors of the vehicle;
identifying, via the processor and based on sensor information in the first output over time and the second output over time, an obstructed sensor from at least one of the first sensor and the second sensor; and
sending, via the processor, a message including information about the obstructed sensor to one or more devices of the vehicle, wherein the sensor information in the first output over time includes a time of flight defining a time for a detection signal emitted by the first sensor to be detected by the first sensor, wherein the first sensor is identified as the obstructed sensor when the time of flight in the first output over time is less than a time of flight minimum threshold, the time of flight minimum threshold being defined as a minimum time of flight for maintaining a desired distance between the first sensor and possible obstructions, wherein the message instructs a sensor cleaning system of the vehicle to clean the obstructed sensor, wherein the sensor cleaning system includes:
an actuator attached to the obstructed sensor that moves the obstructed sensor between a first position and a second position;
a support structure around the obstructed sensor and set back from a wall of the vehicle; and
at least one flexible cleaning member that covers the obstructed sensor in the second position and that bends over the support structure at a location between the obstructed sensor and the support structure, wherein, as the actuator moves the obstructed sensor between the first position and the second position and vice versa, the at least one flexible member cleans the surface of the obstructed sensor.

2. The method of claim 1, wherein identifying the obstructed sensor further comprises:
determining, via the processor, that the first sensor and the second sensor are a same type of sensor;
comparing, via the processor, the first output over time to the second output over time; and
determining, via the processor, at least one difference between the first output over time and the second output over time.

3. The method of claim 2, further comprising:
determining, via the processor, a third output over time for a third sensor of the sensors of the vehicle, wherein the third sensor is a different type of sensor from the first and second sensors;
comparing, via the processor, detection characteristics of the third output over time to detection characteristics for each of the first output over time and the second output over time; and
determining, via the processor, the obstructed sensor is at least one of the first sensor and the second sensor when the detection characteristics of the third output over time fail to match the detection characteristics for the first output over time and/or the second output over time.

4. The method of claim 1, wherein the first sensor is a first imaging sensor and the first output over time includes first computer-generated images of the environment around the portion of the vehicle over time, and wherein the second sensor is a second imaging sensor and the second output over time includes second computer-generated images of the environment around the portion of the vehicle over time.

5. The method of claim 4, wherein identifying the obstructed sensor further comprises:
determining, via the processor, a position and size for targets in the first and second computer-generated images over time, wherein the targets represent objects in the environment around the portion of the vehicle.

6. The method of claim 5, wherein identifying the obstructed sensor further comprises:

determining, via the processor, the obstructed sensor is one of the first sensor or the second sensor when at least one of the targets in one of the first and second computer-generated images over time is not present in the other of the first and second computer-generated images over time.

7. The method of claim 5, wherein identifying the obstructed sensor further comprises:
determining, via the processor and based on the position and size for the targets, a predicted position and size for the targets at a subsequent time.

8. The method of claim 7, wherein identifying the obstructed sensor further comprises:
determining, via the processor, a subsequent position and size for the targets in subsequent first and second computer-generated images over time; and
determining, via the processor, the obstructed sensor is at least one of the first sensor and the second sensor when the subsequent position and size for the targets in the subsequent first and second computer-generated images over time fail to match the predicted position and size for the targets at the subsequent time.

9. A vehicle, comprising:
at least two sensors;
a sensor cleaning system;
a microprocessor coupled to the at least two sensors; and
a computer readable medium coupled to the microprocessor and comprising instructions stored thereon that cause the microprocessor to:
receive output from the at least two sensors monitoring an environment around a portion of the vehicle;
determine a first output over time for a first sensor of the at least two sensors;
determine a second output over time for a second sensor of the at least two sensors;
identify, based on sensor information in the first output over time and the second output over time, an obstructed sensor from at least one of the first sensor and the second sensor; and
send a message including information about the obstructed sensor to one or more devices of the vehicle, wherein the sensor information in the first output over time includes a time of flight defining a time for a detection signal emitted by the first sensor to be detected by the first sensor, wherein the first sensor is identified as the obstructed sensor when the time of flight in the first output over time is less than a time of flight minimum threshold, the time of flight minimum threshold being defined as a minimum time of flight for maintaining a desired distance between the first sensor and possible obstructions, wherein the message instructs the sensor cleaning system to clean the obstructed sensor, wherein the sensor cleaning system includes:
an actuator attached to the obstructed sensor that moves the obstructed sensor between a first position and a second position;
a support structure around the obstructed sensor and set back from a wall of the vehicle; and
at least one flexible cleaning member that covers the obstructed sensor in the second position and that bends over the support structure at a location between the obstructed sensor and the support structure, wherein, as the actuator moves the obstructed sensor between the first position and the second position and vice versa, the at least one flexible member cleans the surface of the obstructed sensor.

10. The vehicle of claim 9, wherein the first sensor is a first imaging sensor and the first output over time includes first computer-generated images of the environment around the portion of the vehicle over time, and wherein the second sensor is a second imaging sensor and the second output over time includes second computer-generated images of the environment around the portion of the vehicle over time.

11. The vehicle of claim 10, wherein in identifying the obstructed sensor the instructions further cause the microprocessor to:
 determine a position and size for targets in the first and second computer-generated images over time, wherein the targets represent objects in the environment around the portion of the vehicle; and
 determine the obstructed sensor is one of the first sensor or the second sensor when at least one of the targets in one of the first and second computer-generated images over time is not present in the other of the first and second computer-generated images over time.

12. A device, comprising:
 a microprocessor; and
 a computer readable medium coupled to the microprocessor and comprising instructions stored thereon that cause the microprocessor to:
  receive output from sensors of a vehicle monitoring an environment around a portion of the vehicle;
  determine a first output over time for a first sensor of the sensors of the vehicle;
  determine a second output over time for a second sensor of the sensors of the vehicle;
  identify, based on sensor information in the first output over time and the second output over time, an obstructed sensor from at least one of the first sensor and the second sensor; and
  send a message including information about the obstructed sensor to one or more devices of the vehicle,
 wherein the sensor information in the first output over time includes a time of flight defining a time for a detection signal emitted by the first sensor to be detected by the first sensor,
 wherein the first sensor is identified as the obstructed sensor when the time of flight in the first output over time is less than a time of flight minimum threshold, the time of flight minimum threshold being defined as a minimum time of flight for maintaining a desired distance between the first sensor and possible obstructions,
 wherein the message instructs a sensor cleaning system of the vehicle to clean the obstructed sensor,
 wherein the sensor cleaning system includes:
  an actuator attached to the obstructed sensor that moves the obstructed sensor between a first position and a second position;
  a support structure around the obstructed sensor and set back from a wall of the vehicle; and
  at least one flexible cleaning member that covers the obstructed sensor in the second position and that bends over the support structure at a location between the obstructed sensor and the support structure,
 wherein, as the actuator moves the obstructed sensor between the first position and the second position and vice versa, the at least one flexible member cleans the surface of the obstructed sensor.

13. The device of claim 12, wherein the instructions cause the microprocessor to render at least a portion of the information about the obstructed sensor to a display device of the vehicle.

* * * * *